(12) United States Patent
Arneson et al.

(10) Patent No.: US 9,730,336 B2
(45) Date of Patent: Aug. 8, 2017

(54) SYSTEM FOR MANUFACTURING A SWALLOWABLE SENSOR DEVICE

(71) Applicant: Innurvation, Inc., Glen Burnie, MD (US)

(72) Inventors: Michael R. Arneson, Finksburg, MD (US); William R. Bandy, Gambrills, MD (US); Roger A. Davenport, Plantation, FL (US); Kevin J. Powell, Annapolis, MD (US); Michael C. Sloan, Ellicott City, MD (US)

(73) Assignee: Innurvation, Inc., Glen Burnie, MD (US)

( * ) Notice: Subject to any disclaimer, the term of this patent is extended or adjusted under 35 U.S.C. 154(b) by 288 days.

(21) Appl. No.: 14/516,191

(22) Filed: Oct. 16, 2014

(65) Prior Publication Data

US 2015/0033552 A1 Feb. 5, 2015

Related U.S. Application Data

(62) Division of application No. 13/408,328, filed on Feb. 29, 2012, now Pat. No. 8,869,390, which is a division
(Continued)

(51) Int. Cl.
*B23P 19/00* (2006.01)
*H05K 3/36* (2006.01)
(Continued)

(52) U.S. Cl.
CPC .............. *H05K 3/36* (2013.01); *A61B 1/0011* (2013.01); *A61B 5/073* (2013.01); *A61B 1/041* (2013.01);
(Continued)

(58) Field of Classification Search
CPC ................ A61B 5/073; A61B 18/1402; A61B 2562/0247; Y10T 29/49146;
(Continued)

(56) References Cited

U.S. PATENT DOCUMENTS 4,844,076 A 7/1989 Lesho et al.
5,279,607 A 1/1994 Schentag et al.
(Continued)

FOREIGN PATENT DOCUMENTS

EP 0 888 888 A2 1/1999
EP 1 211 219 A2 6/2002
(Continued)

OTHER PUBLICATIONS

An International Search Report and Written Opinion dated Dec. 12, 2008 for International Application No. PCT/US08/11326, filed on Sep. 30, 2008 (11 pages).
(Continued)

*Primary Examiner* — Thiem Phan
(74) *Attorney, Agent, or Firm* — Sterne, Kessler, Goldstein & Fox P.L.L.C.

(57) ABSTRACT

Methods and systems for manufacturing a swallowable sensor device are disclosed. Such a method includes mechanically coupling a plurality of internal components, wherein the plurality of internal components includes a printed circuit board having a plurality of projections extending radially outward. A cavity is filled with a potting material, and the mechanically coupled components are inserted into the cavity. The cavity may be pre-filled with the potting material, or may be filled after the mechanically coupled components have been inserted therein. A distal end of each projection abuts against a wall of the cavity thereby preventing the potting material from covering each distal end. The cavity is sealed with a cap causing the potting
(Continued)

material to harden within the sealed cavity to form a housing of the swallowable sensor device, wherein the distal end of each projection is exposed to an external environment of the swallowable sensor device.

13 Claims, 25 Drawing Sheets

Related U.S. Application Data of application No. 11/865,464, filed on Oct. 1, 2007, now abandoned.

(51) Int. Cl.
*A61B 1/00* (2006.01)
*A61B 1/04* (2006.01)
*A61B 5/07* (2006.01)
*H05K 1/14* (2006.01)

(52) U.S. Cl.
CPC .............. *A61B 5/07* (2013.01); *H05K 1/144* (2013.01); *Y10T 29/49002* (2015.01); *Y10T 29/49004* (2015.01); *Y10T 29/4913* (2015.01); *Y10T 29/49117* (2015.01); *Y10T 29/49124* (2015.01); *Y10T 29/49126* (2015.01); *Y10T 29/49146* (2015.01); *Y10T 29/5313* (2015.01); *Y10T 29/53022* (2015.01); *Y10T 29/53252* (2015.01)

(58) Field of Classification Search
CPC ........... Y10T 29/5313; Y10T 29/53252; G01L 19/149; A61M 31/002
USPC ......... 29/757, 705, 729, 760, 787, 801, 829, 29/830, 841; 600/101, 160, 373, 459, 600/476
See application file for complete search history.

(56) References Cited

U.S. PATENT DOCUMENTS

| | | |
|---|---|---|
| 5,329,498 A | 7/1994 | Greenstein |
| 5,395,366 A | 3/1995 | D'Andrea et al. |
| 5,794,226 A | 8/1998 | Yoneyama |
| 5,833,603 A | 11/1998 | Kovacs et al. |
| 5,992,769 A | 11/1999 | Wise et al. |
| 6,022,482 A | 2/2000 | Chen et al. |
| 6,093,330 A | 7/2000 | Chong et al. |
| 6,240,312 B1 | 5/2001 | Alfano et al. |
| 6,249,346 B1 | 6/2001 | Chen et al. |
| 6,310,642 B1 | 10/2001 | Adair et al. |
| 6,330,464 B1 | 12/2001 | Colvin et al. |
| 6,357,865 B1 | 3/2002 | Kubby et al. |
| 6,362,512 B1 | 3/2002 | Kubby et al. |
| 6,379,989 B1 | 4/2002 | Kubby et al. |
| 6,399,405 B1 | 6/2002 | Chen et al. |
| 6,428,469 B1 | 8/2002 | Iddan et al. |
| 6,431,175 B1 | 8/2002 | Penner et al. |
| 6,462,391 B1 | 10/2002 | Chong et al. |
| 6,465,856 B2 | 10/2002 | Gulvin et al. |
| 6,473,361 B1 | 10/2002 | Chen et al. |
| 6,479,311 B1 | 11/2002 | Scharf et al. |
| 6,479,315 B1 | 11/2002 | Zosel et al. |
| 6,486,588 B2 | 11/2002 | Doron et al. |
| 6,504,286 B1 | 1/2003 | Porat et al. |
| 6,506,620 B1 | 1/2003 | Scharf et al. |
| 6,510,275 B1 | 1/2003 | Tran et al. |
| 6,577,893 B1 | 6/2003 | Besson et al. |
| 6,584,348 B2 | 6/2003 | Glukhovsky |
| 6,608,679 B1 | 8/2003 | Chen et al. |
| 6,658,179 B2 | 12/2003 | Kubby et al. |
| 6,661,070 B2 | 12/2003 | Zosel et al. |
| 6,662,448 B2 | 12/2003 | Kubby et al. |
| 6,720,709 B2 | 4/2004 | Porat et al. |
| 6,764,446 B2 | 7/2004 | Wolinsky et al. |
| 6,861,341 B2 | 3/2005 | Chen et al. |
| 6,936,003 B2 | 8/2005 | Iddan |
| 6,944,316 B2 | 9/2005 | Glukhovsky et al. |
| 6,950,690 B1 | 9/2005 | Meron et al. |
| 6,959,130 B2 | 10/2005 | Fauver et al. |
| 6,984,205 B2 | 1/2006 | Gazdzinski |
| 7,076,284 B2 | 7/2006 | Segawa et al. |
| 7,104,952 B2 | 9/2006 | Iddan et al. |
| 7,118,529 B2 | 10/2006 | Glukhovsky et al. |
| 7,118,531 B2 | 10/2006 | Krill |
| 7,122,001 B2 | 10/2006 | Uchiyama et al. |
| 7,135,342 B2 | 11/2006 | Colvin, Jr. et al. |
| 7,140,766 B2 | 11/2006 | Glukhovsky et al. |
| 7,142,908 B2 | 11/2006 | Glukhovsky |
| 7,160,258 B2 | 1/2007 | Imran et al. |
| 7,164,572 B1 | 1/2007 | Burdon et al. |
| 7,195,588 B2 | 3/2007 | Homan et al. |
| 7,201,872 B2 | 4/2007 | Meron |
| 7,226,146 B2 | 6/2007 | Chen et al. |
| 7,245,954 B2 | 7/2007 | Glukhovsky |
| 7,336,833 B2 | 2/2008 | Horn |
| 7,354,397 B2 | 4/2008 | Fujita et al. |
| 7,365,509 B2 | 4/2008 | Park et al. |
| 8,500,630 B2 | 8/2013 | Gilad et al. |
| 8,869,390 B2 | 10/2014 | Arneson et al. |
| 2001/0023523 A1 | 9/2001 | Kubby et al. |
| 2002/0107444 A1 | 8/2002 | Adler |
| 2002/0130916 A1 | 9/2002 | Gulvin et al. |
| 2002/0138009 A1 | 9/2002 | Brockway et al. |
| 2002/0188323 A1 | 12/2002 | Penner et al. |
| 2002/0192542 A1 | 12/2002 | Luski et al. |
| 2002/0192852 A1 | 12/2002 | Scharf et al. |
| 2002/0193669 A1 | 12/2002 | Glukhovsky |
| 2002/0197762 A1 | 12/2002 | Zosel et al. |
| 2002/0198470 A1 | 12/2002 | Imran et al. |
| 2003/0018280 A1 | 1/2003 | Lewkowicz et al. |
| 2003/0055339 A1 | 3/2003 | Fujii et al. |
| 2003/0077223 A1 | 4/2003 | Glukhovsky et al. |
| 2003/0086641 A1 | 5/2003 | Kubby et al. |
| 2003/0092964 A1 | 5/2003 | Kim |
| 2003/0139661 A1 | 7/2003 | Kimchy et al. |
| 2003/0162375 A1 | 8/2003 | Chen et al. |
| 2003/0174208 A1 | 9/2003 | Glukhovsky et al. |
| 2003/0195400 A1 | 10/2003 | Glukhovsky |
| 2003/0195415 A1 | 10/2003 | Iddan |
| 2003/0201696 A1 | 10/2003 | Muramatsu et al. |
| 2003/0214579 A1 | 11/2003 | Iddan |
| 2003/0216622 A1 | 11/2003 | Meron et al. |
| 2004/0002056 A1 | 1/2004 | Lorens et al. |
| 2004/0032957 A1 | 2/2004 | Mansy et al. |
| 2004/0054278 A1 | 3/2004 | Kimchy et al. |
| 2004/0073087 A1 | 4/2004 | Glukhovsky et al. |
| 2004/0084745 A1 | 5/2004 | Chen et al. |
| 2004/0109488 A1 | 6/2004 | Glukhovsky et al. |
| 2004/0114856 A1 | 6/2004 | Kubby et al. |
| 2004/0122315 A1 | 6/2004 | Krill |
| 2004/0145738 A1 | 7/2004 | Sun et al. |
| 2004/0162469 A1 | 8/2004 | Imran |
| 2004/0171915 A1 | 9/2004 | Glukhovsky et al. |
| 2004/0181155 A1 | 9/2004 | Glukhovsky |
| 2004/0193029 A1 | 9/2004 | Glukhovsky |
| 2004/0204744 A1 | 10/2004 | Penner et al. |
| 2004/0236182 A1 | 11/2004 | Iddan et al. |
| 2004/0258328 A1 | 12/2004 | Adler |
| 2005/0009415 A1 | 1/2005 | Johnson |
| 2005/0052796 A1 | 3/2005 | Camwell et al. |
| 2005/0065441 A1 | 3/2005 | Glukhovsky |
| 2005/0075555 A1 | 4/2005 | Glukhovsky et al. |
| 2005/0095790 A1 | 5/2005 | Chen et al. |
| 2005/0107666 A1 | 5/2005 | Glukhovsky et al. |
| 2005/0143624 A1 | 6/2005 | Iddan |
| 2005/0256430 A1 | 11/2005 | Lewkowicz et al. |
| 2005/0259487 A1 | 11/2005 | Glukhovsky et al. |
| 2005/0266074 A1 | 12/2005 | Zilberstein et al. |
| 2005/0272974 A1 | 12/2005 | Iddan |
| 2006/0004256 A1 | 1/2006 | Gilad et al. |
| 2006/0114291 A1 | 6/2006 | Chen et al. |

(56) References Cited

U.S. PATENT DOCUMENTS

| | | |
|---|---|---|
| 2006/0155174 A1 | 7/2006 | Glukhovsky et al. |
| 2006/0163680 A1 | 7/2006 | Chen |
| 2006/0173361 A1 | 8/2006 | Gorden |
| 2006/0193505 A1 | 8/2006 | Glukhovsky et al. |
| 2006/0224040 A1 | 10/2006 | Khait et al. |
| 2006/0232164 A1 | 10/2006 | Kondo et al. |
| 2006/0241422 A1 | 10/2006 | Muratayev et al. |
| 2007/0002604 A1 | 1/2007 | Lin et al. |
| 2007/0078335 A1 | 4/2007 | Horn |
| 2007/0123772 A1 | 5/2007 | Euliano et al. |
| 2007/0167813 A1 | 7/2007 | Lee et al. |
| 2007/0167826 A1 | 7/2007 | Lee et al. |
| 2007/0171693 A1 | 7/2007 | Koyama et al. |
| 2007/0213659 A1 | 9/2007 | Trovato et al. |
| 2007/0260133 A1 | 11/2007 | Meyer |
| 2008/0077440 A1 | 3/2008 | Doron |
| 2008/0146871 A1 | 6/2008 | Arneson et al. |
| 2008/0208174 A1 | 8/2008 | Johnson et al. |
| 2009/0088618 A1 | 4/2009 | Arneson et al. |
| 2009/0306633 A1 | 12/2009 | Trovato et al. |
| 2009/0311193 A1 | 12/2009 | Mauro et al. |
| 2011/0105864 A1 | 5/2011 | Robertson et al. |
| 2011/0130658 A1 | 6/2011 | Iddan |
| 2012/0153981 A1 | 6/2012 | Arneson et al. |

FOREIGN PATENT DOCUMENTS

| | | |
|---|---|---|
| EP | 1 213 259 A2 | 6/2002 |
| EP | 1 213 260 A2 | 6/2002 |
| EP | 1 243 550 A2 | 9/2002 |
| EP | 1 310 808 A2 | 5/2003 |
| EP | 1 339 101 A2 | 8/2003 |
| WO | WO 01/53792 A2 | 7/2001 |
| WO | WO 03/010967 A1 | 2/2003 |
| WO | WO 2004/014227 A1 | 2/2004 |
| WO | WO 2004/054430 A2 | 7/2004 |
| WO | WO 2004/059568 A1 | 7/2004 |
| WO | WO 2004/112567 A2 | 12/2004 |
| WO | WO 2005/060348 A2 | 7/2005 |
| WO | WO 2006/059331 A2 | 6/2006 |
| WO | WO 2006/116718 A2 | 11/2006 |
| WO | WO 2007/028035 A2 | 3/2007 |
| WO | WO 2007/035445 A1 | 3/2007 |

OTHER PUBLICATIONS

International Preliminary Report on Patentability issued Apr. 7, 2010, directed toward related International Application No. PCT/US08/11326, The International Bureau of WIPO, Geneva, Switzerland; 8 pages.

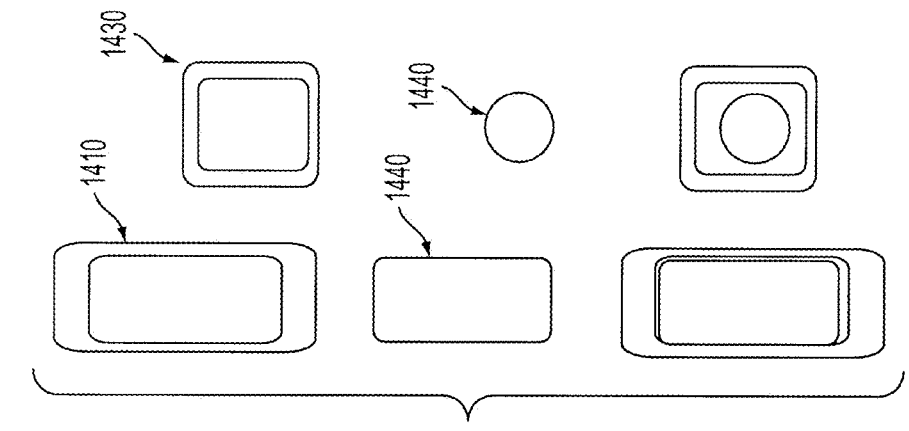
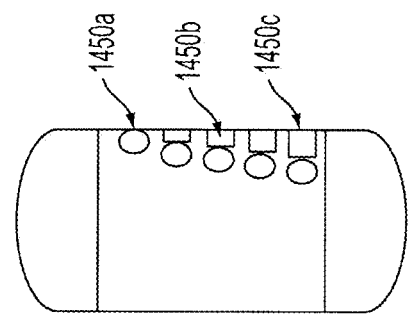
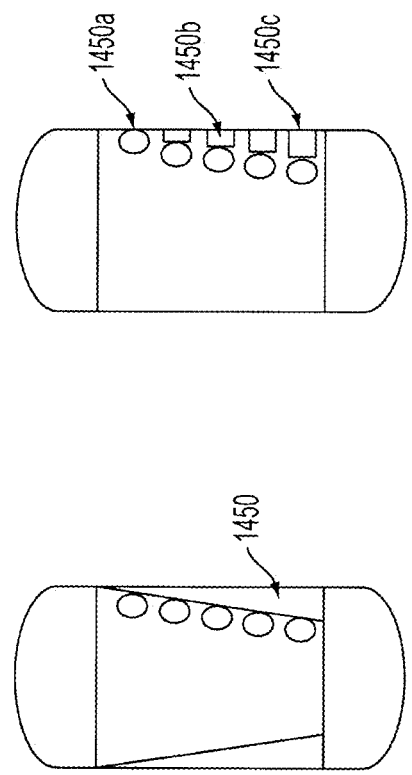
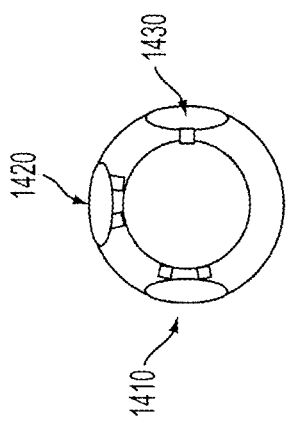

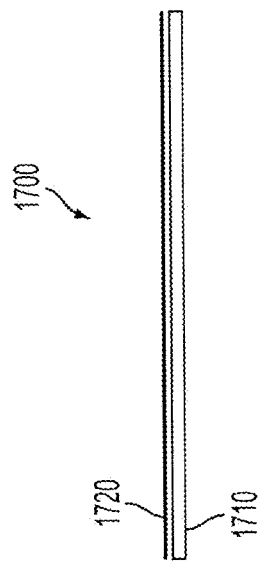
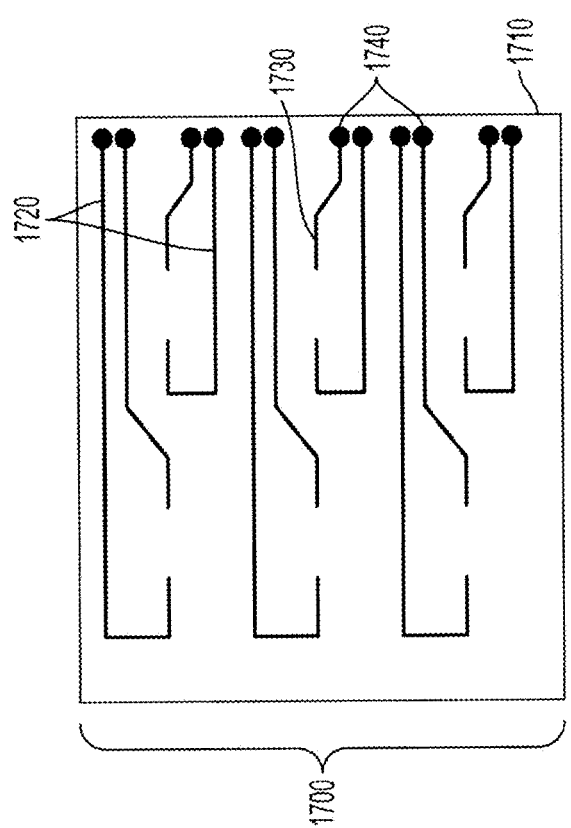

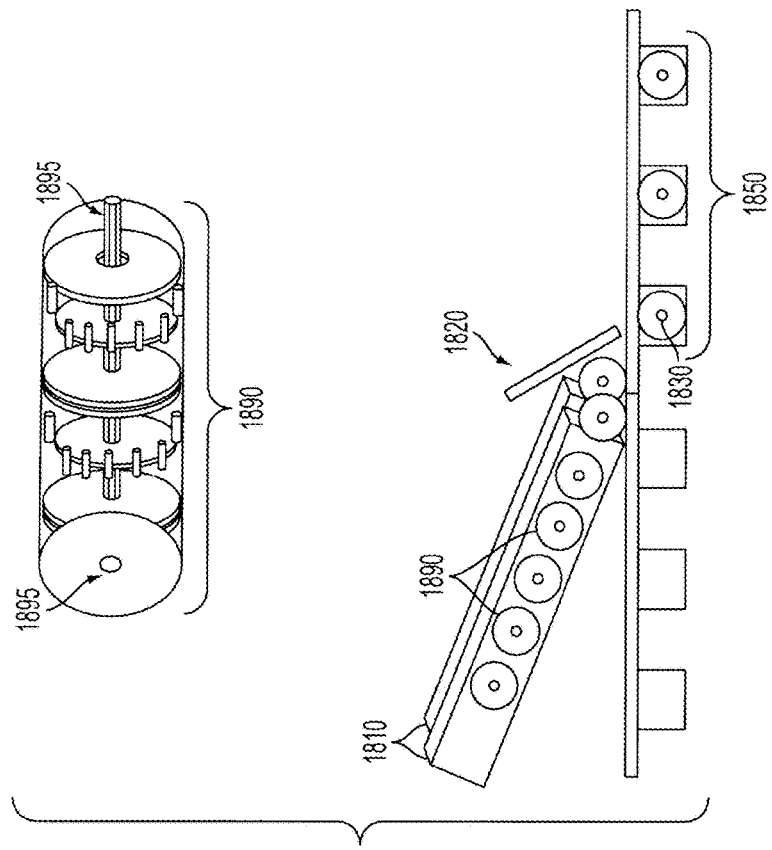
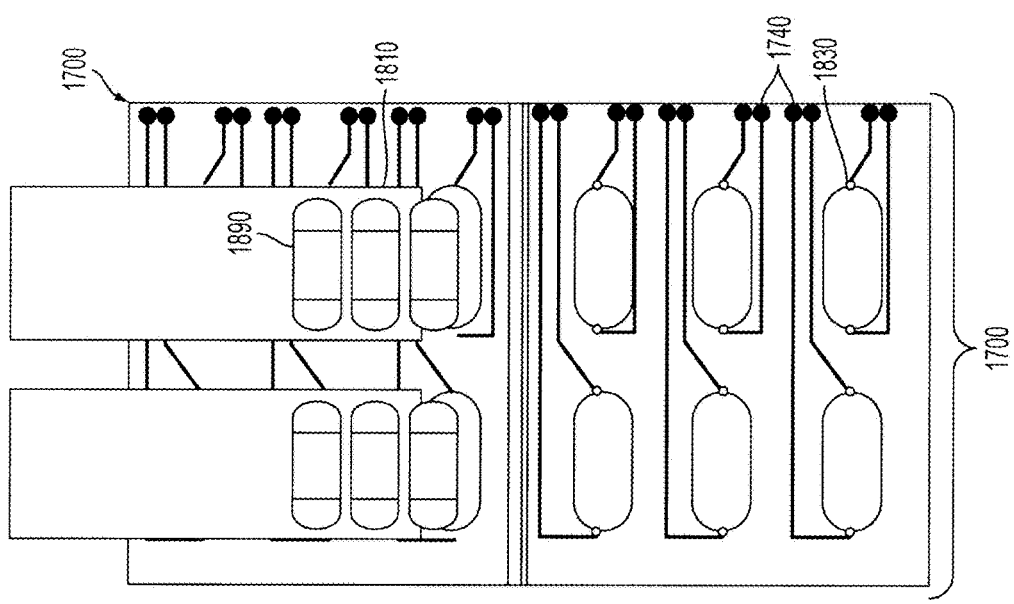
FIG. 18B
FIG. 18A

SYSTEM FOR MANUFACTURING A SWALLOWABLE SENSOR DEVICE

CROSS REFERENCE TO RELATED APPLICATIONS

This application is a divisional of U.S. application Ser. No. 13/408,328, filed Feb. 29, 2012, which will issue as U.S. Pat. No. 8,869,390 on Oct. 28, 2014, which is a divisional of U.S. application Ser. No. 11/865,464, filed Oct. 1, 2007, now abandoned, all of which are hereby incorporated by reference in its entirety.

BACKGROUND OF THE INVENTION

1. Field of the Invention

The present invention relates to medical diagnostics, and in particular, to swallowable medical diagnostic devices.

2. Background Art

The population of the United States is aging. The first wave of the 78 million "Baby Boomers" is beginning to turn 60 years old. There has been an explosion in diabetes cases, estimated at 194 million cases worldwide today, and predicted to reach 350 million cases by year 2025. Obesity currently affects two thirds of the U.S. population. There is a rising incidence of cardiac problems for women (the number one cause of death for women). Hepatitis C will soon reach epidemic levels, infecting nearly 5 million people, more than the number of people infected with AIDS in the U.S. Thus, simple and easy diagnostic and treatment techniques are needed, especially because many of the diseases that afflict the population are chronic, requiring repeat testing and treatment over time.

Such diagnostic and treatment techniques may be realized by using a swallowable sensor device that is ingested by a patient. The swallowable sensor device could be used to sense a condition and/or deliver medical treatment as it travels through the patient's gastrointestinal tract.

However, conventional swallowable sensor devices have several drawbacks. One drawback of conventional swallowable sensor devices is that they are quite large. In fact, conventional swallowable sensor devices are so large that a portion of the patient population cannot even swallow these devices. Even if a patient could swallow a conventional swallowable sensor device, its large size could cause it to become lodged in the patient's gastrointestinal tract, which would require surgery to remove.

Another problem with conventional swallowable sensor devices is that they use a radio frequency (RF) signal platform to communicate with external entities. The extent to which RF signals cause harm to human tissue is not fully understood. The potential for harm only increases as the source of the RF signals comes closer to human tissue. As a result, many patients are apprehensive about ingesting conventional swallowable sensor devices.

Given the foregoing, what is needed is an improved swallowable sensor device, and a method for manufacturing such a swallowable sensor device.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

FIGS. 4, 5, 6, 6A, 6B, and 7 illustrate various manners in which internal components of a swallowable sensor device are mechanically and/or electrically coupled to each other in accordance with embodiments of the present invention.

Figure 8:
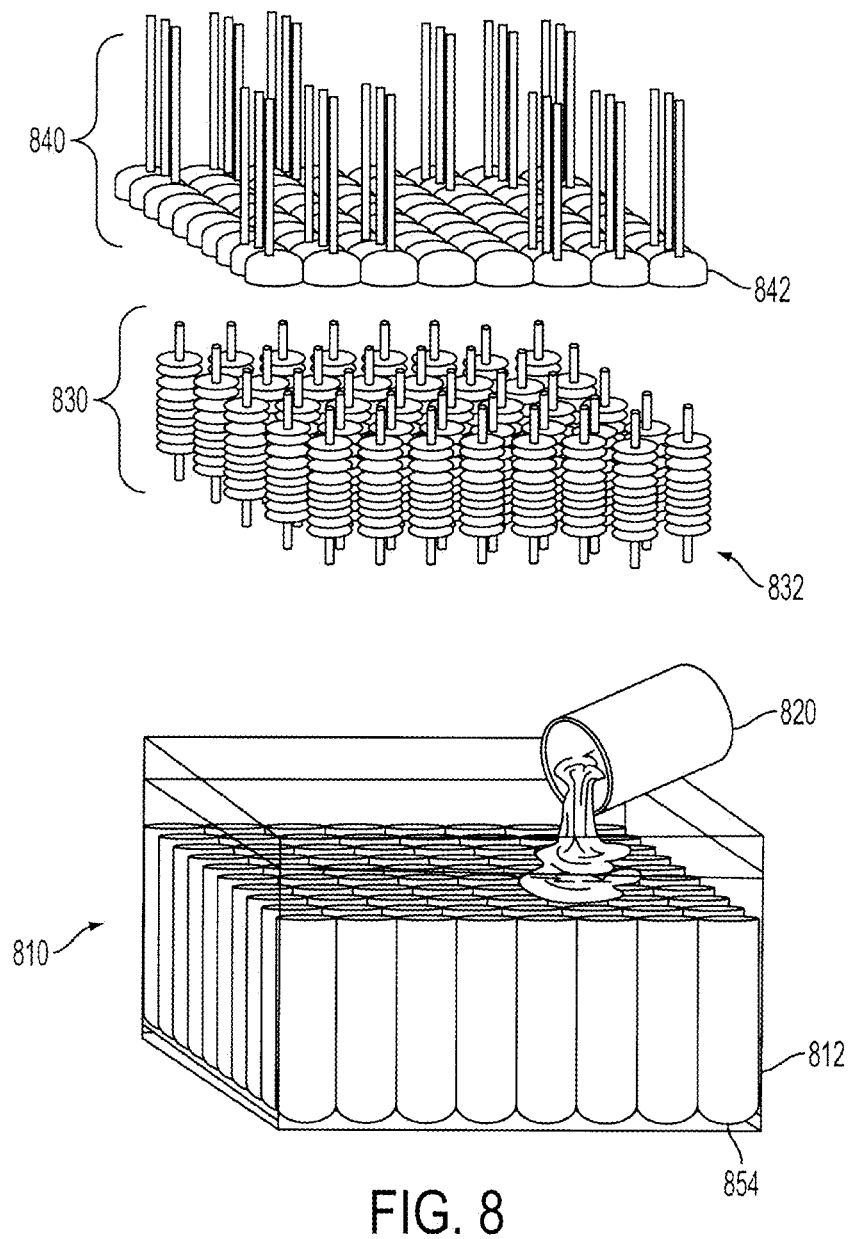

FIG. 8 illustrate example molds used for manufacturing a swallowable sensor device in accordance with an embodiment of the present invention.

Figure 9A:
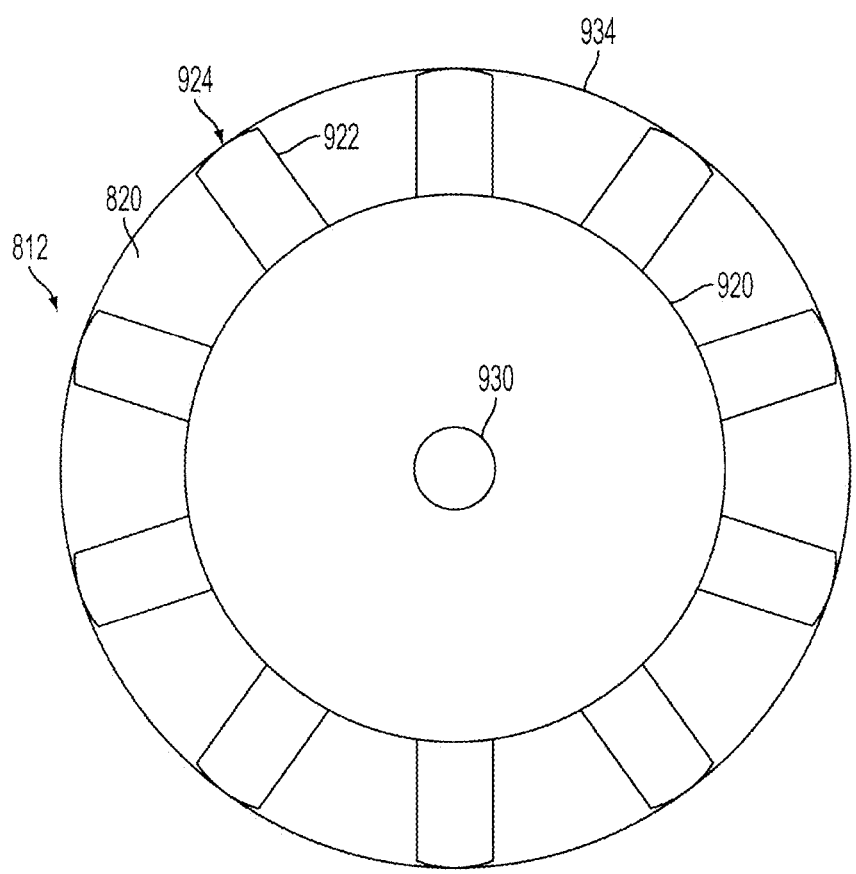
Figure 9B:
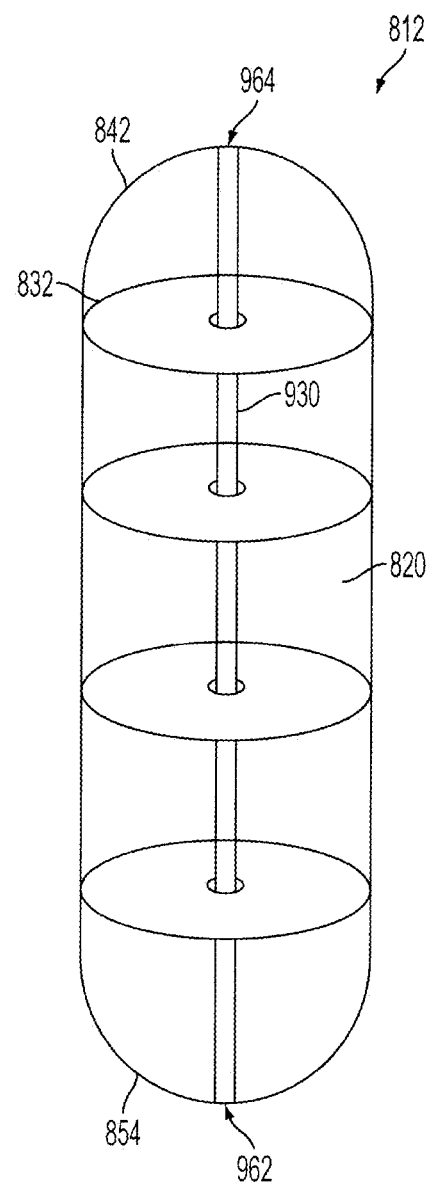

FIGS. 9A and 9B respectively illustrate a cross-sectional view and side view of internal components of a swallowable sensor device disposed in a mold in accordance with an embodiment of the present invention.

Figure 10:
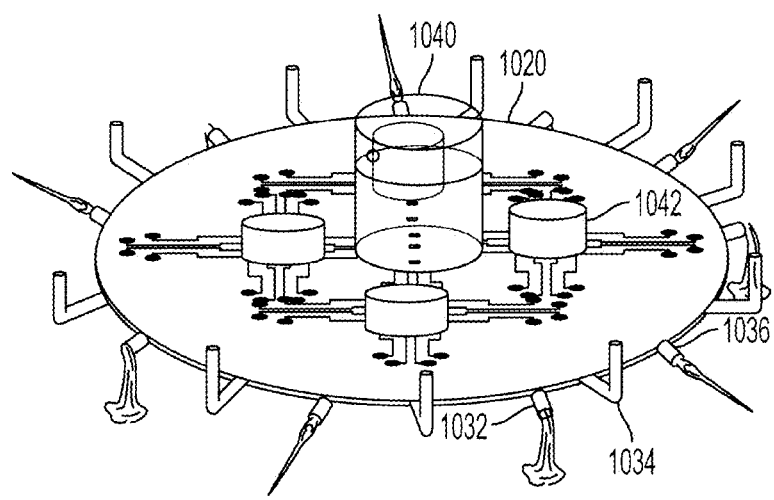

FIG. 10 illustrates an example printed circuit board in accordance with an embodiment of the present invention.

Figure 11:
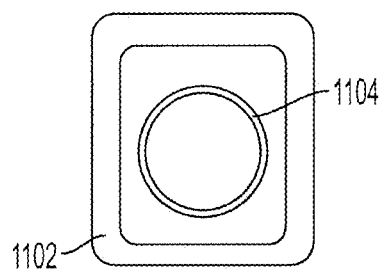

FIG. 11 illustrates an example sensor in accordance with an embodiment of the present invention.

Figure 12:
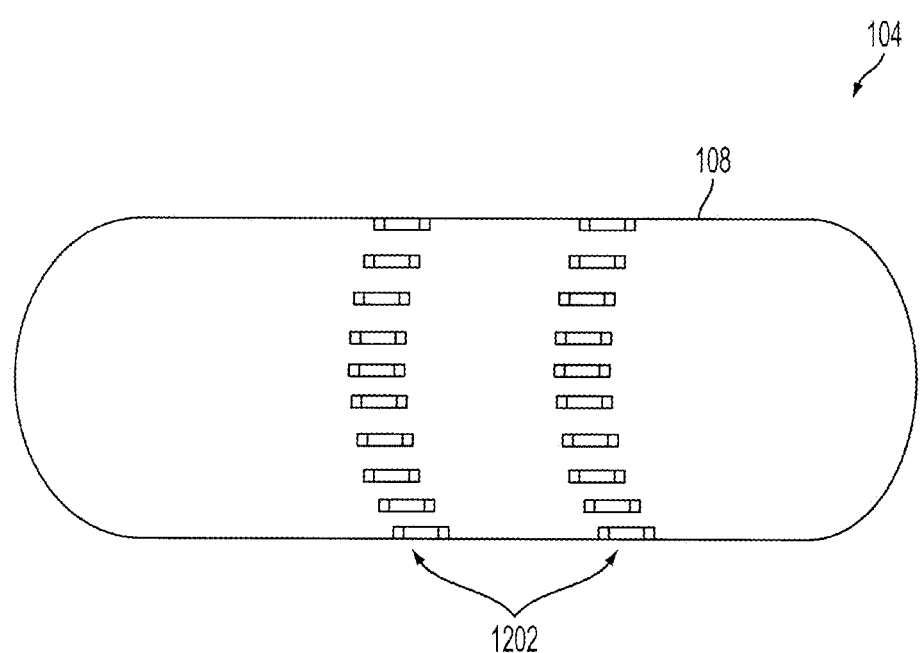

FIG. 12 illustrates a swallowable sensor including a plurality of sensors in accordance with an embodiment of the present invention.

Figure 13:
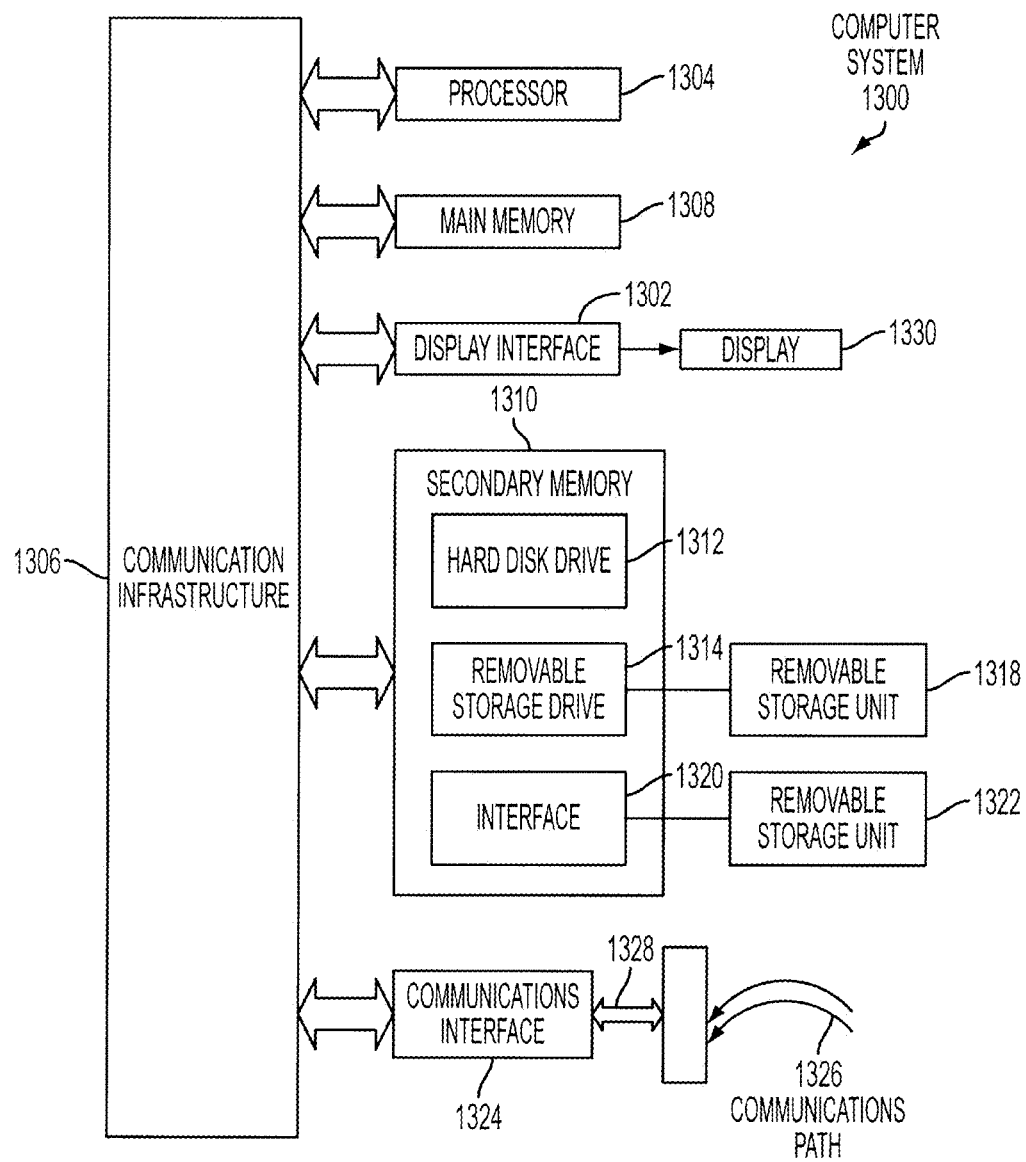

FIG. 13 illustrates an exemplary computer system useful for implementing an embodiment of the present invention.

FIGS. 14A-D illustrate a swallowable sensor according to another embodiment of the present invention.

FIGS. 15A-D depict several configurations of time released biological sensors according to embodiments of the present invention.

Figure 16:
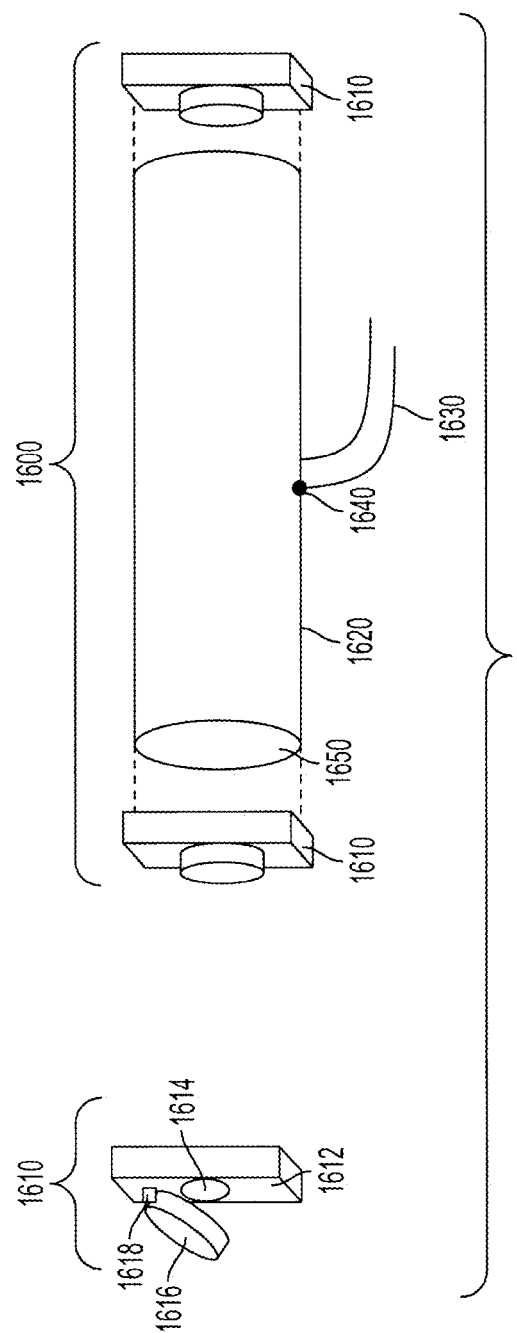

FIG. 16 depicts an example micro-pump according to an embodiment of the present invention.

FIGS. 17A-D illustrate an example packaging assembly according to embodiments of the present invention.

FIGS. 18A-B illustrate a machine that uses the example packaging assembly of

FIGS. 17A-D.

Figure 19:
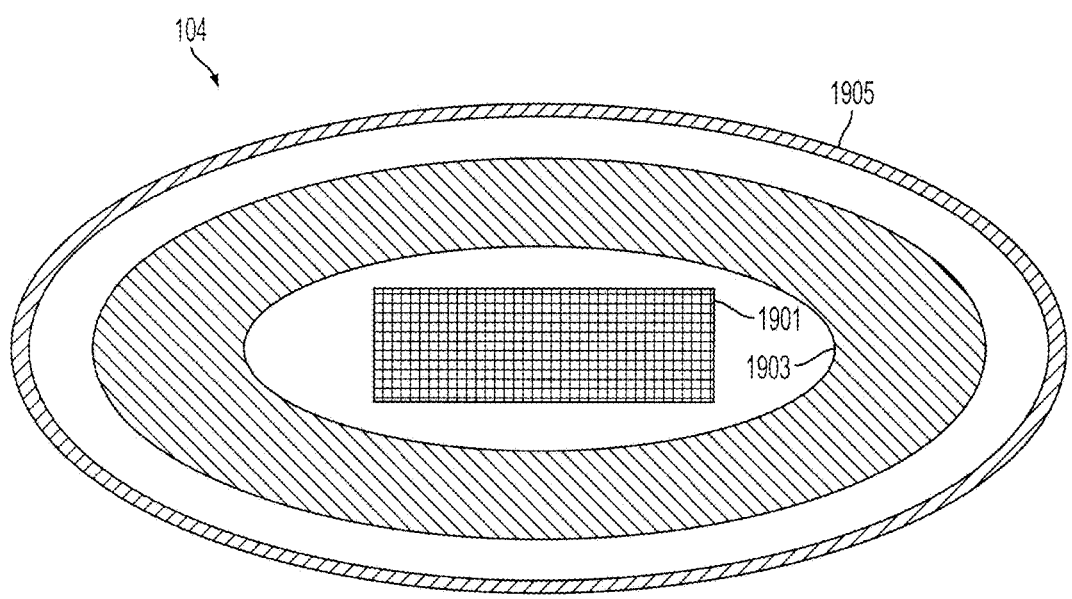
Figure 20:
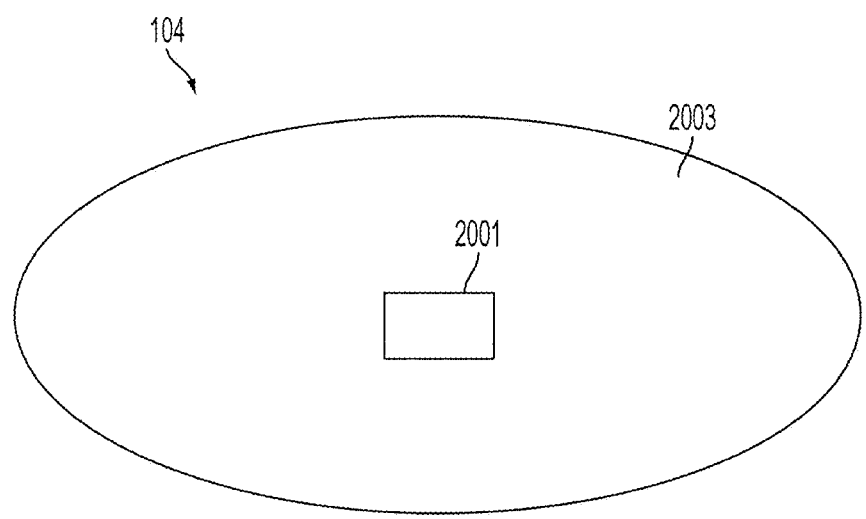

FIGS. 19 and 20 illustrate a swallowable sensor device having a layered structure for efficient power transfer according to embodiments of the present invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

I. Overview

Described herein are methods and systems for manufacturing a swallowable sensor device, and applications thereof. In the specification, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

A swallowable sensor device manufactured in accordance with an embodiment of the present invention is relatively small compared to conventional swallowable sensor devices. In addition, a swallowable sensor device manufactured in accordance with an embodiment of the present invention uses acoustic frequencies, rather than RF frequencies, to communicate with an external entity (such as a computer or hand-held device). As a result, the swallowable sensor device may be ingested by a patient for diagnostic or treatment purposes. To diagnose the patient, the swallowable sensor device may collect data and/or samples as it travels through the gastrointestinal tract of the patient. To treat the patient, the swallowable sensor device may deliver medication or other types of treatment at specific locations within the patient's body. Similarly, the swallowable sensor device may deliver material to augment a particular sensor device or an external diagnostic procedure, such as a dye, marker, or radioactive isotope.

The diagnostic and treatment functionalities are performed by diagnostic/treatment components of the swallowable sensor device. The diagnostic/treatment components are exposed to the external environment of the swallowable sensor device. For example, sensors of the swallowable sensor device are exposed to fluids and acids within the patient's gastrointestinal tract in order to collect data regarding the patient's internal body chemistry. Similarly, treatment delivery components are exposed to the external environment of the swallowable sensor device in order to deliver certain types of treatment to the patient.

Circuitry contained within the swallowable sensor device controls the implementation of the diagnostic and/or treatment functionalities. Although the diagnostic/treatment components are coupled to the circuitry, the circuitry and other internal components (such as a power supply, a communication module, and other such components) are not exposed to the external environment. Exposing the circuitry and other internal components to the external environment would likely cause the swallowable sensor device to malfunction, and/or could also be harmful to the patient.

To expose the diagnostic/treatment components, while protecting the internal components, an embodiment of the present invention uses a molding technique to manufacture a swallowable sensor device. In this embodiment, the internal components of the swallowable sensor device—such as a printed circuit (PC) board, a battery, and a transducer—are mechanically and electrically coupled to each other. The internal components are inserted into a molding cavity. The cavity may be pre-filled with a potting material or the potting material may be injected into the cavity after the internal components have been inserted therein. The cavity is then sealed, allowing the potting material to harden. The hardened potting material forms an exterior housing that protects the internal components of the swallowable sensor device from the external environment.

In an embodiment, the potting material comprises a UV curable epoxy. In this embodiment, the chemical composition of the potting material results in an acoustically transmissive substance (transmissive at a desired acoustic frequency) with an impedance between that of a transducer and the human body. Furthermore, curing the UV epoxy in an oxygen rich environment results in a layering of the cure, which in turn results in a layering of the impedance from the potting material abutting the transducer and the external layer of the swallowable sensor device. Ideally, the swallowable sensor device includes an infinite number of layers from the acoustic impedance of the transducer to the acoustic impedance of the human body, resulting in the highest possible acoustic performance (i.e., the most energy transmitted outward from the acoustic source). Accordingly, embodiments of the present invention include a relatively large number of layers of acoustic impedance between the transducer and the human body. The aforementioned layered impedance construction yields a highly efficient swallowable sensor device in acoustic performance.

Importantly, the PC board includes a plurality of projections that extend radially outward causing them to abut against the cavity wall. Because the projections abut against the cavity wall, the potting material is prevented from covering the distal ends of the projections. As a result, when the potting material hardens to form the exterior housing, the projections will be exposed to the then external environment. However, the projections will be mechanically and/or electrically coupled to the internal components of the swallowable sensor device.

Each projection may comprise an electrode or a hollow tubing. The electrodes are coupled to sensors that collect data corresponding to the internal body chemistry of a patient. Because the housing does not cover the electrodes, the sensors will be exposed to the external environment of the swallowable sensor device, but electrically coupled to internal components. Thus, the sensors can properly function to receive stimuli from the external environment, which can then be communicated to internal circuitry contained within the swallowable sensor device.

Additionally, each sensor may be covered with a digestible, protective material. As the swallowable sensor device travels through a human's gastrointestinal tract, the protective material covering each sensor is digested. By covering the sensors with different thicknesses of protective material, the sensors can be exposed to the external environments at different times as the swallowable sensor device travels through a human's gastrointestinal tract. Thus, the swallowable sensor device can be configured for timed release of each sensor based on the thickness of the digestible, protective material covering each sensor.

Similar to each electrode, a first end of the hollow tubing is exposed to the external environment and a second end is coupled to a container that is sealed within the housing of the swallowable sensor device. Thus, the hollow tubing can properly function to deliver materials and treatment to and/or collect samples from the external environment of the swallowable sensor device.

The methods and systems of the present invention for manufacturing a swallowable sensor device are described in greater detail below. To better understand these methods and systems, however, it is first helpful to describe an example environment in which such a swallowable sensor device may be implemented and an example swallowable sensor device.

II. An Example Environment

Figure 1:
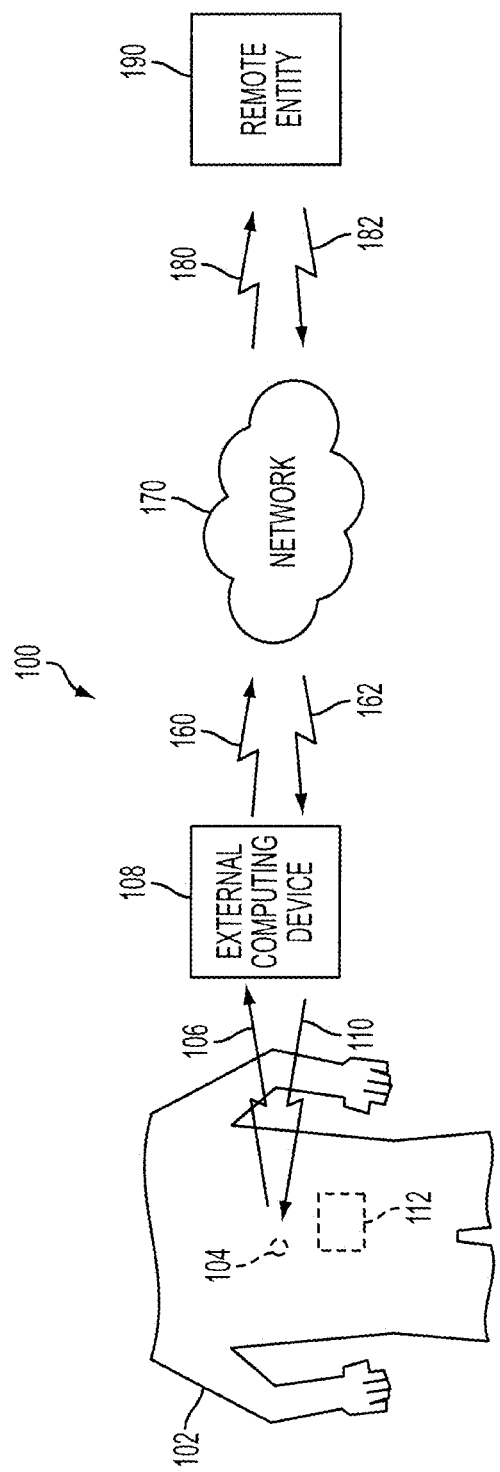
FIG. 1 illustrates an example environment in which a swallowable sensor device may operate in accordance with an embodiment of the present invention.

FIG. 1 shows an example environment 100 in which a swallowable sensor device 104 may be used in accordance with an embodiment of the present invention. Environment 100 includes a human 102, a swallowable sensor device 104, an external computing device 108, and optionally includes a network 170 and a remote entity 190. As illustrated in FIG. 1, swallowable sensor device 104 is disposed in human 102. Swallowable sensor device 104 is configured to sense one or more attributes or conditions of, and/or deliver medical treatment or materials to, human 102 as swallowable sensor device 104 passes through human 102, as described for example in U.S. Patent Application No. 60/842,360 to Arneson et al., entitled "Swallowable Low Power Sensor Device and System for Communication with Same" and filed Sep. 6, 2006, the entirety of which is incorporated by reference herein.

While passing through human 102, swallowable sensor device 104 transmits information in a communication signal 106 to be received outside human 102. As shown in FIG. 1, external computing device 108 may receive communication signal 106. Computing device 108 may be used to display the information received in communication signal 106, to interact with the information, to process the information, and/or to transmit the information (raw or processed) to another entity. Example systems and methods for transmitting data from swallowable sensor device 104 to external computing device 108 are described, for example, in U.S. Provisional Patent Application No. 60/941,184 to Arneson et al., entitled "System and Method for Acoustic Data Transmission Involving a Swallowable Low Power Sensor Device" and filed May 31, 2007; U.S. patent application Ser. No. 11/851,214 to Arneson et al., entitled "System and Method for Acoustic Data Transmission Involving a Swallowable Low Power Sensor Device" and filed Sep. 6, 2007; U.S. patent application Ser. No. 11/851,236 to Arneson et al., entitled "System and Method for Acoustic Data Transmission" and filed Sep. 6, 2007; and U.S. patent application Ser. No. 11/896,946 to Arneson et al., entitled Methods and Systems for Acoustic Data Transmission and filed Sep. 6, 2007. The entirety of each of the foregoing applications is incorporated by reference herein.

In an embodiment, computing device 108 can interact with swallowable sensor device 104 by transmitting a communication signal 110. Such interaction may be used to control functions of swallowable sensor device 104 and/or to image at a desired resolution an internal portion of a patient, as described for example in U.S. Provisional Patent Application No. 60/924,928 Arneson et al., entitled "Imaging and Locating Systems and Methods for a Swallowable Sensor Device" and filed Jun. 5, 2007, and U.S. patent application Ser. No. 11/851,179 to Arneson et al., entitled "Imaging and Locating Systems and Methods for a Swallowable Sensor Device" and filed Sep. 6, 2007. The entirety of each of the foregoing applications is incorporated by reference herein.

In embodiments, human 102 may be provided with one or more swallowable sensor devices 104 that human 102 may swallow at designated times and/or periodically to perform an analysis of one or more health-related conditions of human 102.

Computing device 108 may be configured to communicate with remote entity 190 using wired and/or wireless links, in a direct fashion or through network 170. For example, computing device 108 transmits a communication signal 160 to network 170, which transmits a communication signal 180 to remote entity 190. Network 170 may be any type of network or combination of networks, such as a telephone network (e.g., a land line and/or cellular network), a personal area network (PAN), a local area network (LAN), and/or a wide area network (WAN) such as the Internet.

Remote entity 190 may be one or more of a variety of entities, including a human and/or computer-based entity. For example, remote entity 190 may include a doctor who receives information collected by swallowable sensor device 104 (and optionally processed by computer device 108) in communication signal 180.

Remote entity 190 may send a return communication to computing device 108 via network 170. For example, a return communication signal 182 is transmitted by remote entity 190 to network 170, which transmits a return communication signal 162 to computing device 108. In this manner, remote entity 190 (e.g., doctor and/or computer system) can provide feedback to computing device 108 in communication signal 182 regarding the analysis of human 102 performed by swallowable sensor device 104. Return communication signal 182 may include any type of data/ information format for providing the feedback, including an email, a text message, a text file, a document formatted for commercially available word processing software, a proprietary document/data format, auditory alarms, alerts and messages, etc. In addition, computing device 108 may send instructions to swallowable sensor device 104 in communication signal 110 based on the feedback provided from remote entity 190 via network 170.

Swallowable sensor device 104 may optionally communicate with computing device 108 via an intermediate sensor link module 112. Sensor link module 112 may receive communication signal 106 from swallowable sensor device 104. Sensor link module 112 transmits a communication signal (not shown) to computing device 108 on a wired or wireless connection, to provide the information sensed by swallowable sensor device 104 to computing device 108. For example, sensor link module 112 may be used when swallowable sensor device 104 communicates using an acoustic communications signal having a power level too low to reliably be received by computing device 108.

In another embodiment, sensor link module 112 may provide a communication interface between swallowable sensor device 104 and network 170, such that a separate computing device 108 is not required. In such an embodiment, sensor link module 112 may perform some or all functions of computing device 108 described above, and thus sensor link module 112 may be referred to as a computing device. For example sensor link module 112 may receive communication signal 106 from and transmit communication signal 110 to swallowable sensor device 104.

Multiple sensor link modules 112 may provide a capability of accurately locating swallowable sensor device 104 as it travels through human 102. Example locating systems and methods are described in the aforementioned U.S. Provisional Patent Application No. 60/924,928 to Arneson et al., entitled "Imaging and Locating Systems and Methods for a Swallowable Sensor Device" and filed Jun. 5, 2007, and U.S. patent application Ser. No. 11/851,179 to Arneson et al., entitled "Imaging and Locating Systems and Methods for a Swallowable Sensor Device" and filed Sep. 6, 2007. The entirety of each of the foregoing applications is incorporated by reference herein.

As shown in FIG. 1, sensor link module 112 is coupled to human 102. In an embodiment, multiple sensor link modules 112 may be attached to human 102 at various locations in order to receive the interior acoustic signal from different angles. Sensor link module 112 may be, for example, directly attached to the skin of human 102, such as by an adhesive strap, an integrated flexible fabric assembly such as a belt or girdle. Sensor link module 112 may be attached to human 102 in one or more locations, including the head, neck, chest, back, abdomen, arm, leg, etc. With regard to receiving communication signal 106 from swallowable sensor device 104 passing through the gastrointestinal tract, sensor link module 112 may be attached to the neck, chest, back, and/or abdomen for a short signal path.

III. An Example Swallowable Sensor Device

Figure 2A:
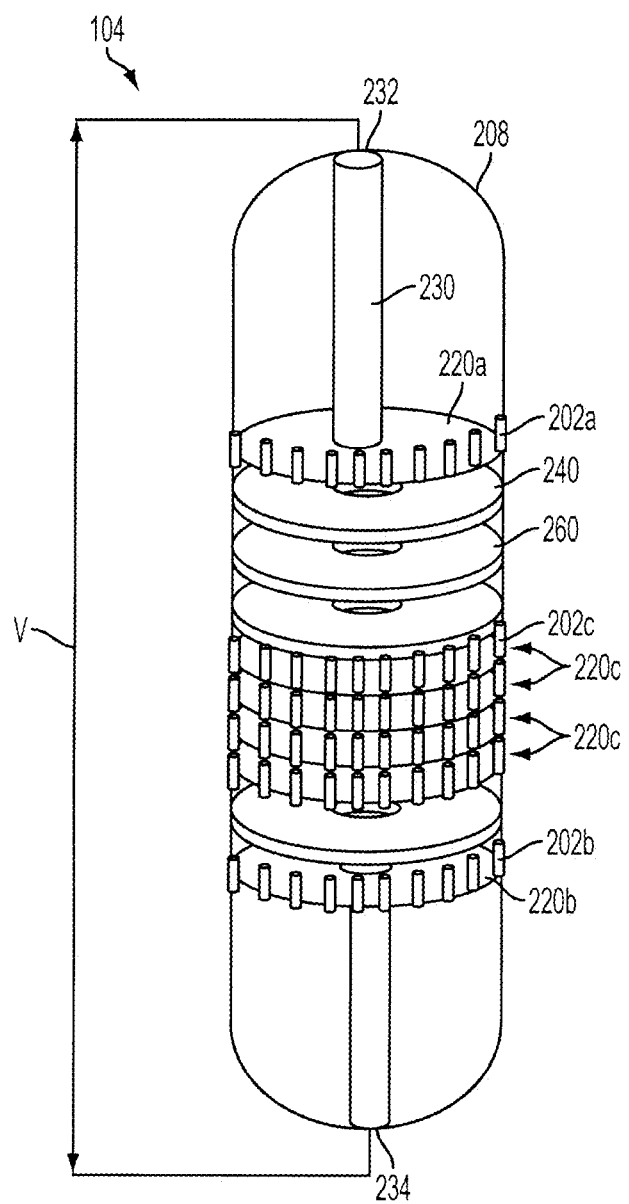
FIGS. 2A and 2B illustrate example embodiments of a swallowable sensor.
Figure 2B:
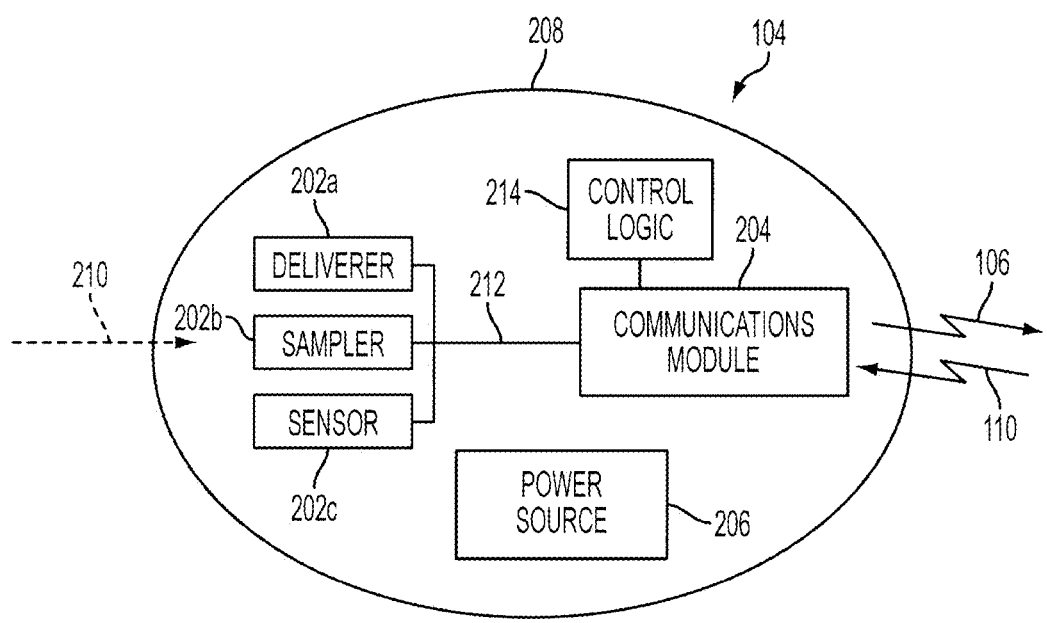

FIGS. 2A and 2B illustrate swallowable sensor device 104 according to embodiments of the present invention. FIG. 2A illustrates structural components of swallowable sensor device 104. FIG. 2B is a block diagram illustrating functional components of swallowable sensor device 104. Each of these figures is described in more detail below.

Referring to FIG. 2A, swallowable sensor device 104 includes a housing 208 that holds a plurality of internal components, including printed circuit (PC) boards 220a-c, a transducer (transmitter) 240, and a battery 260. In the embodiment illustrated in FIG. 2A, the plurality of internal components are mechanically and electrically coupled to each other by a post 230. In other embodiments, the plurality of internal components are mechanically and electrically coupled using other means, as illustrated for example in FIGS. 4-7.

Housing 208 may be the size of a vitamin or other type of pill that is swallowable by humans. For example, housing 208 may be approximately 1 mm to 10 mm in diameter and approximately 4 mm to 25 mm in length, and preferably approximately 5 mm in diameter and approximately 14 mm in length. Housing 208 may be any suitable shape, including oval, elliptical, capsule shaped, or spherical. The small size of housing 208 allows swallowable sensor device 104 to be easily ingested by an average human 102. The small size overcomes difficulties present with conventional swallowable sensor devices, which are often so large that only a small percentage of the population can actually swallow them safely. Further, the small size of housing 208 allows swallowable sensor device 104 to pass completely through the digestive system of a human 102 without becoming trapped due to size incompatibilities or blockage (growths) along the way.

Housing 208 may be made from a variety of non-digestible or slow rate of digestion materials. Such materials may include, but are not limited to, the following materials: a plastic material (such as a resin, a resinoid, a polymer or polymer matrix, a cellulose derivative); a casein material; a protein; a metal (including a combination of metals/alloy); a glass material; a ceramic; a composite material; an enteric coating; and/or other material/combination of materials. In an embodiment, housing 208 may be comprised of a material that aids in the sensing of biological, chemical, or other attributes of body material that touches or comes in close proximity to the housing 208, such as could be called an integrated housing and sensor material. Furthermore, in an embodiment, housing 208 comprises primarily a non-digestible material with orifices or indentations which are filled with a layer of digestible material of variable thickness covering a sensor material that is in turn deposited on top of an electrically conductive pathway to internal components.

Swallowable sensor device 104 also includes treatment/diagnostic components 202, such as a treatment delivery component 202a, a sample receiver component 202b, and a sensor 202c. Treatment/diagnostic components 202 are coupled to PC boards 220a-c, but are not contained within materials comprising housing 208. In other words, treatment/diagnostic components 202 are exposed to the external environment of swallowable sensor device 104 in order to deliver treatment and/or collect data as swallowable sensor device travels through the gastrointestinal tract of human 102. Treatment delivery component 202a is configured to deliver treatment (such as medication, radiation therapy, or another form of treatment or therapy) to human 102. Sample receiver component 202b is configured to receive one or more samples (such as digestive fluid, stomach acid, tissue, or some other sample) from human 102. Sensor 202c is used to sense (e.g., measure, detect, etc.) a received stimulus 210. Swallowable sensor device 104 can include any number of sensors 202c, each of which may all sense the same condition or may sense a different condition than another sensor 202c. In an embodiment, a molding technique is used to seal the internal components within housing 208, while exposing treatment/sensor components to the external environment—as described in more detail below.

In an embodiment, the treatment/sensor components may be covered by a digestible, protective material. By applying different thicknesses of protective material, the treatment/sensor components can be released at different times corresponding to the amount of time it takes to digest the protective material, as described in more detail below.

A first end 232 and a second end 234 of post 230 are also exposed to the external environment of swallowable sensor device 104. A voltage and/or signal may be applied across first end 232 and second end 234, after swallowable sensor device 104 is fabricated, to test whether swallowable sensor device 104 is functioning properly, as described in more detail below.

FIG. 2B is a block diagram illustrating functional components of swallowable sensor device 104 in accordance with an embodiment of the present invention. Although FIG. 2B illustrates swallowable sensor device 104 as having only three treatment/diagnostic components 202, one of skill in the art will recognize that treatment/diagnostic components 202 may be included, but are not limited to, a plurality of treatment deliver components 202a, a plurality of sample receiver components 202b, and/or a plurality of sensors 202c, as illustrated in FIG. 2A. Treatment/diagnostic components 202 send output to, or receive input from, communications module 204 via an electrical coupling 212. Communications module 204 may comprise PC boards 220 and transducer 240 of FIG. 2A. Electrical coupling 212 may comprise an electrical trace disposed one or more PC boards 220, an electrical trace or traces disposed on a post 230 in electrical contact with electrical traces on PC board 220, a wireless communication link, or some other type of electrical coupling.

Communications module 204 receives the output from treatment/diagnostic components 202 and generates communication signal 106 to include data based on the output. Communication signal 106 is transmitted from swallowable sensor device 104. Communications module 204 may also receive communication signal 110 transmitted from external computing device 108.

In an embodiment, communication signal 106 comprises an acoustic signal. In this embodiment, communications module 204 includes one or more transducers (such as transducer 240) that are configured to convert electrical energy to mechanical energy, and vice versa. For example, the one or more transducers convert the electrical energy received from treatment/diagnostic components 202 into the mechanical energy of acoustic communication signal 106, and convert the mechanical energy of acoustic communication signal 110 into electrical energy sent to communications module 204, control logic 214, or treatment/diagnostic components 202. Example methods and systems for transmitting data from swallowable sensor device 104 are described, for example, in the aforementioned U.S. Provisional Patent Application No. 60/941,184 to Arneson et al., entitled "System and Method for Acoustic Data Transmission Involving a Swallowable Low Power Sensor Device" and filed May 31, 2007; U.S. patent application Ser. No. 11/851,214 to Arneson et al., entitled "System and Method for Acoustic Data Transmission Involving a Swallowable Low Power Sensor Device" and filed Sep. 6, 2007; U.S. patent application Ser. No. 11/851,236 to Arneson et al., entitled "System and Method for Acoustic Data Transmission" and filed Sep. 6, 2007; and U.S. patent application Ser. No. 11/896,946 to Arneson et al., entitled Methods and Systems for Acoustic Data Transmission and filed Sep. 6, 2007. The entirety of each of the foregoing applications is incorporated by reference herein.

Swallowable sensor device 104 also includes control logic 214, which may be used to gate or control swallowable sensor device 104. Control logic 214 may be included on one or more PC boards 220. Control logic 214 may operate in a sub-threshold voltage (Vt) manner (e.g., to save power), or may operate in normal bias modes. In an embodiment, swallowable sensor device 104 is an autonomous device with one way communication (transmission capability), so that control logic 214 may be extremely simple, and thus would not consume much power even when operating in normal bias modes. In another embodiment, swallowable sensor device 104 may communicate in both directions—i.e., it may be configured to transmit information to and receive instructions from computing device 108 and/or sensor link module 112. Control logic 214 may thus have additional complexity in order to, for example, decode and implement received instructions.

Swallowable sensor device 104 also includes power source 206. Power source 206 provides power (e.g., via electrical energy) to operate the components of swallowable sensor device 104 that require power, such as communications module 204 and/or sensor 202. Power source 206 may include, for example and without limitation, battery 260 of FIG. 2A, a liquid or gel surrounding communications module 204, an energy harvesting module, or some other power source.

In an embodiment, swallowable sensor device 104 is configured for low power operation, including extreme low power (XLP) operation. To achieve XLP operation, swallowable sensor device 104 can use one or both of a very small battery and energy harvesting to operate swallowable sensor device 104. In an embodiment, circuits of swallowable sensor device 104 are implemented on one or more integrated circuits (ICs), in a technology such as CMOS, or other technology. The IC(s) and any other internal components of swallowable sensor device 104 are mounted to one or more PC boards 220 of FIG. 2A. Thus, in embodiments, power source 206 is configured for low power output, including supplying power in the milliwatt and microwatt ranges. Such low power requirements enable the size of power source 206 to be minimal.

In a CMOS embodiment, MOSFET circuits may be configured to operate in a deep sub-threshold voltage (sub-Vt) mode, which lowers their switching time to acoustic switching frequencies, and lowers their power consumption by orders of magnitude. In such a mode the MOSFET devices operate as analog devices. Such operation was demonstrated in the mid-1980's by Carver Meade with regard to eye and ear chips. Such a mode of operation eliminates the need for digitizing the sensor data, which can be very power intensive, and which further reduces the power consumption by a large factor.

After being swallowed by human 102, swallowable sensor device 104 eventually passes from human 102, such as when human 102 has a bowel movement to excrete waste. In an embodiment, swallowable sensor device 104 is disposable.

It may be useful to have positive confirmation if and when sensor device 104 has been excreted. In some humans 102, sensor device 104 may not pass through the digestive tract within an average life time of sensor device 104. In an embodiment, a power source 206 (FIG. 2B) may be of limited supply. When this power source is below a predetermined level, control logic may cease all activities except for an occasional short communications signal with proportionally large amounts of time not transmitting nor processing. The communications signal is intended to be as short as possible to achieve lowest power consumption, but long enough to determine location. An external computing device 108 may then be able to determine a location and path of a last transmission to determine the likelihood of an excretion. Optionally, a sensor link module 112 is located in, on, or around the bowl of a toilet. This configuration signals excretion of a sensor device, and is an embodiment for recovering swallowable sensor device 104 when having an acoustic transmission. Since a toilet bowl is filled with water, the acoustic signals 106 will transmit across the medium.

In another embodiment, swallowable sensor device 104 may be recovered (and recycled) for reuse. Depending upon the ability or control of the patient, swallowable sensor device 104 may alternatively be inserted into a lower gastrointestinal tract of human 102 as a suppository device. In a further embodiment, sensor device 104 may also be placed within a female reproductive tract. In this further embodiment, sensor device 104 is configured to sense body temperature, hormonal levels, cancer markers, and a variety of STDs. This embodiment is a potential aid to conception and/or reproductive disease and cancer diagnoses.

Depending on the configuration of sensor 202, while passing through human 102, swallowable sensor device 104 can sense conditions and/or features of any part of the gastrointestinal tract or contents thereof, and any of the materials/fluids contained within and/or secreted by the organs in the gastrointestinal tract or organs indirectly associated with the gastrointestinal tract. Swallowable sensor device 104 can deliver treatment to patient 102. Swallowable sensor device 104 can also receive conditions or signals from even more remote body organs such as acoustic pickup of heartbeat and/or breathing and more indirect conditions such as temperature. In an embodiment, an imager device is contained within swallowable sensor device 104 to allow visual observation of the gastrointestinal tract of human 102.

Having presented a description of an example environment and swallowable sensor device, a method for manufacturing such a swallowable sensor device is now described.

IV. Method for Manufacturing a Swallowable Sensor Device

A. Overview

Figure 3:
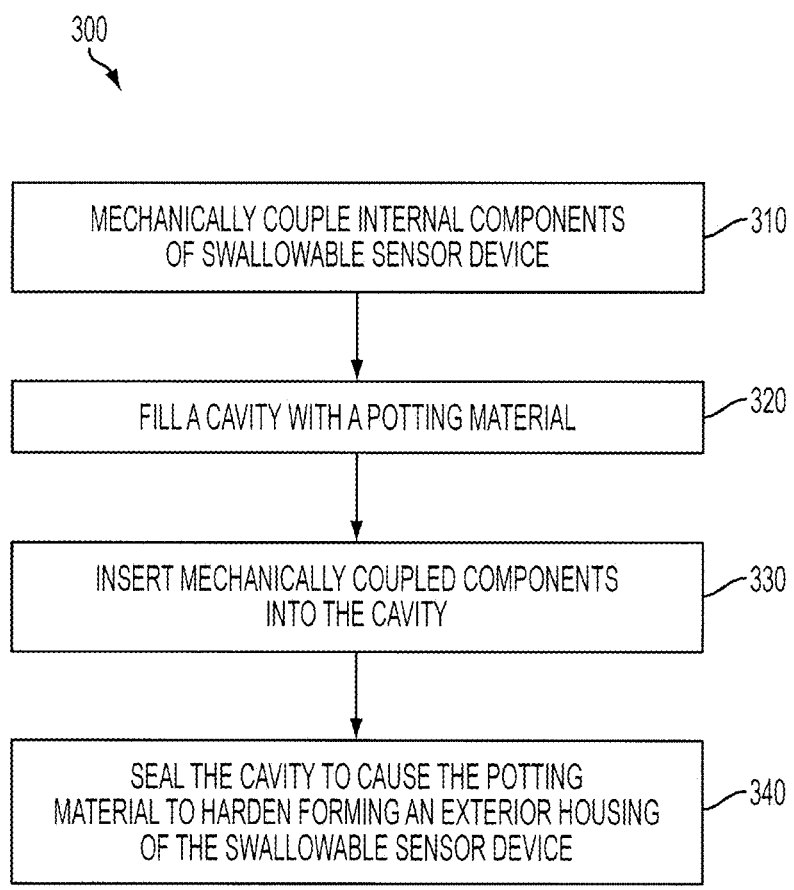
FIG. 3 illustrates an example method for manufacturing a swallowable sensor device in accordance with an embodiment of the present invention.

FIG. 3 depicts a block diagram 300 illustrating an overview of an example method for manufacturing a swallowable sensor device in accordance with an embodiment of the present invention. Block diagram 300 begins at a step 310 in which internal components of a swallowable sensor device are mechanically coupled. The internal components may include, for example, PC boards 220, transducer 240, and battery 260 of FIG. 2A. Other example internal components are described below. As described in more detail below (see FIGS. 4-7), the internal components may be mechanically and/or electrically coupled together using a variety of techniques—including using a central post, using outer posts, stacking the internal components, and/or a combination of these techniques.

In a step 320, a cavity is filled with a potting material, and in a step 330, the mechanically coupled components are inserted in the cavity. In an embodiment, step 320 occurs before step 330. In another embodiment, step 320 occurs after step 330. In other words, the cavity may be pre-filled with the potting material. Alternatively, the mechanically coupled components can be inserted into the cavity, and then the potting material can be injected therein. The potting material may include, but is not limited to, the following materials: a plastic material (such as a resin, a resinoid, a polymer, a cellulose derivative); a casein material; a protein; a glass material; a ceramic; a composite material; and/or other materials or combinations of materials.

In a step 340, the cavity is sealed with a cap. The cap contains the potting material, forming the entire outside shape. The cavity may be passive to UV, allowing UV curing potting materials to harden quickly. The cavity may also simply contain the potting material while it hardens without external influence. The internal components include a PC board having a plurality of projections. As set forth above and described in more detail below, the projections abut against a wall of the cavity, thereby preventing the potting material from covering a distal end of each projection. As a result, the distal ends are exposed to an external environment of the swallowable sensor device upon the completion of the hardening of the potting materials.

B. Example Mechanical And Electrical Couplings

Figure 4:
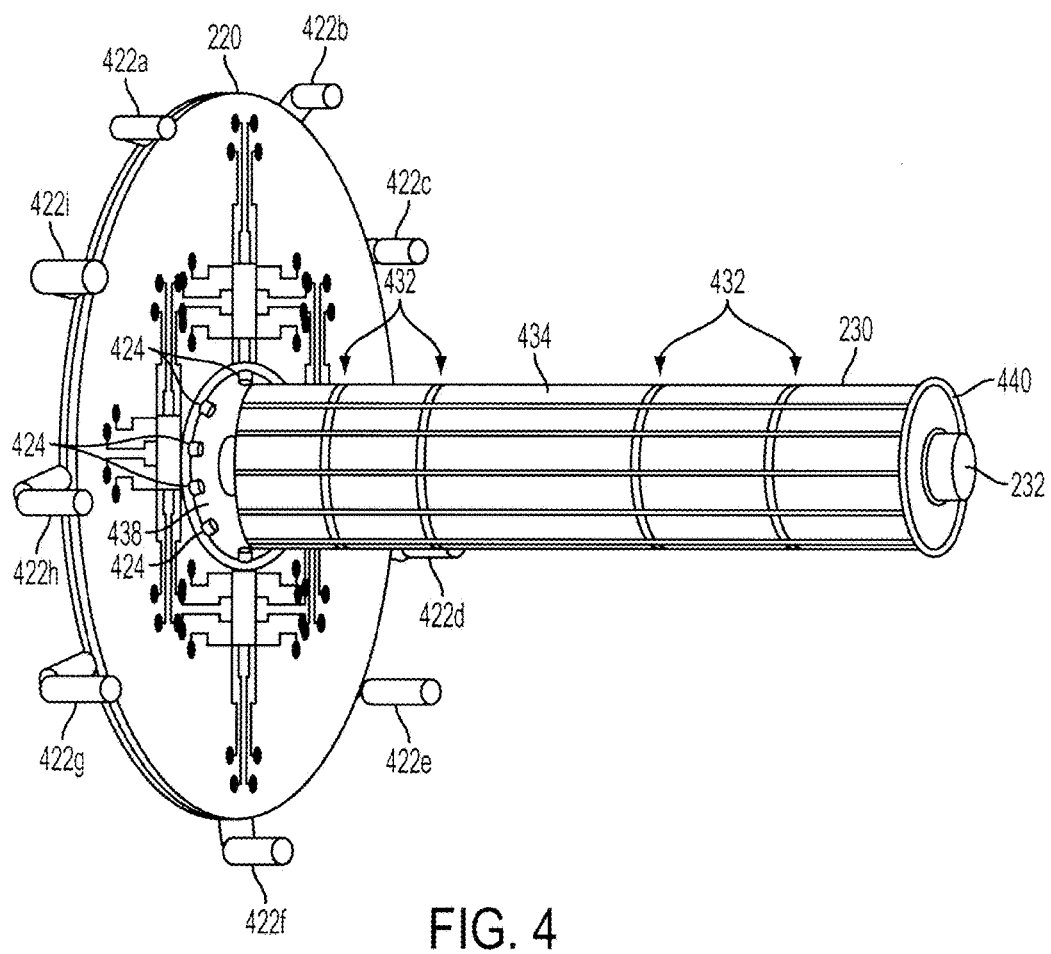

The mechanical and electrical coupling of the internal components is now described with reference to FIGS. 4-7. FIG. 4 illustrates an example manner for mechanically and electrically coupling the internal components, such as PC board 220, using central post 230. In the embodiment illustrated in FIG. 4, PC board 220 is annularly-shaped and includes a plurality of projections 422a-i that extend radially outward. As described herein, projection 422 may comprises an electrode and/or a hollow tubing. Examples of electrode 422 include a wire (straight or bent), a flat metal bushing, a plated PC board surface, or even a non-conductive covering to an electrical connection that can be easily remove after the hardening of the potting material. Similarly, examples of hollow tubings 422 include a glass tube, a plastic tube, a metal tube, a tube manufactured from electrical-mechanical materials such as with a transducer 240 (but in a different shape), a rod of material that is removed after the potting materials harden, or the like. These examples illustrate a few functions, and do not limit the scope of this invention by any exclusion. PC board 220 also includes an inner opening 438 having a plurality of knobs 424 that extend radially inward. Knobs 424 may each independently be mechanical and/or electrical in function.

Post 230 includes a plurality of grooves 432 encircling its exterior. Post 230 may also include traces 434 that are disposed on the exterior. The interior of post 230 includes an insulator layer 440 and a central conductor 232. In one embodiment, central insulator layer 440 may comprise a transducer that is configured to convert electrical energy to mechanical energy. Additionally or alternatively, an annularly-shaped transducer may be coupled to post 230 by inserting post 230 into the inner opening of the annularly-shaped transducer 240, as illustrated for example in FIG. 2A.

PC board 220 is mechanically coupled to post 230 by inserting post 230 in opening 438. In an embodiment, post 230 and opening 438 are keyed such as not to be able to assemble in an incorrect configuration. As post 230 is inserted into opening 438 of PC board 220, inner knobs 424 are urged into one of the grooves 432 providing a mechanical coupling and mechanical spacing as appropriate. In another embodiment, grooves 432 are not required as mechanical spacing can be attained from spacing materials deposited onto PC board 220, transducer 240 and the like. Additionally, traces 434 come into electrical contact with inner knobs 424 providing an electrical coupling between PC board 220 and post 230. Other internal components, such as a battery and transducer, are mechanically and electrically coupled to post 230 in a similar manner.

Figure 5:
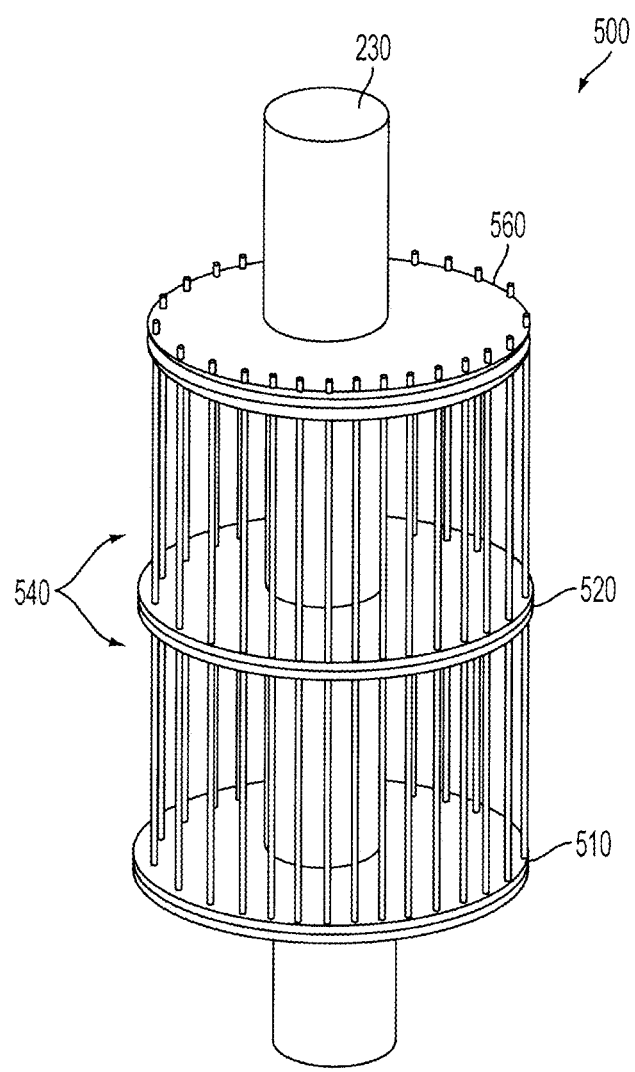

FIG. 5 illustrates another example manner for mechanically and electrically coupling internal components in accordance with an embodiment of the present invention. The internal components illustrated in FIG. 5 include a battery 560, a first PC board 520, and a second PC board 510. Central post 230 provides mechanical coupling along a common central axis of first PC board 510, second PC board 520, and battery 560. Electrical coupling between first PC board 510, second PC board 520, and battery 560 is provided by outer posts 540.

Figure 6:
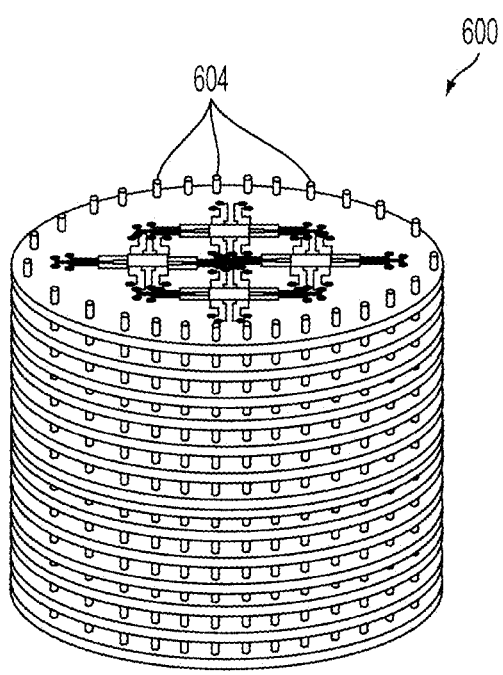

FIG. 6 illustrates a further example manner for mechanically and electrically coupling internal components of swallowable sensor device 104 in accordance with an embodiment of the present invention. FIG. 6 illustrates a stack 600 of components including PC boards, transducers, batteries, and sensors. Each PC board includes a plurality of spacers 604. Spacers 604 provide mechanical and/or electrical coupling between the PC boards in stack 600.

Figure 6A:
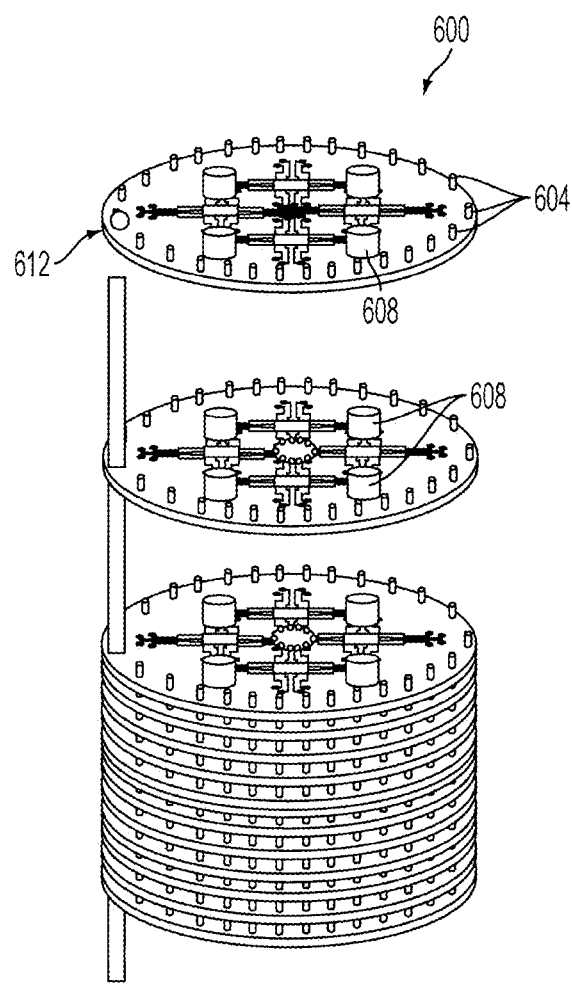

FIG. 6A illustrates a further refinement of FIG. 6. FIG. 6A illustrates a series of conductive paths 604, with a keyed or absent location 612 to assure correct alignment during assembly of a stack of components 600. An example of a keyed location 612 is a larger conductor, for example a conductor for ground. An example of an absent location is a missing hole in the position of 612 assuring no conductor penetrates that location. Furthermore, spacers 608 provide mechanical alignment from board to board, assuring parallel placement, proper electrical isolation, and optionally sonic or ultrasonic signal isolation between boards in stack 600. In this embodiment, spacers 608 do not need extremely accurate placement, unlike conductors which typically require accurate alignment to be properly inserted into a hole.

The assembly of stack 600 illustrated in FIG. 6A may include the following steps: (i) prepare each board with affixing spacers 608; (ii) select a large conductor of length as long or longer than stack 600 in finality; (iii) place boards onto the large conductor one at a time, aligning the large conductor with keyed hole 612; (iv) insert current assembly into a tapered tube or another fixture having an internal diameter equal to the diameter of boards 600; and (v) insert conductors 604 through the entire assembly 600 while aligned by previous step.

Figure 6B:
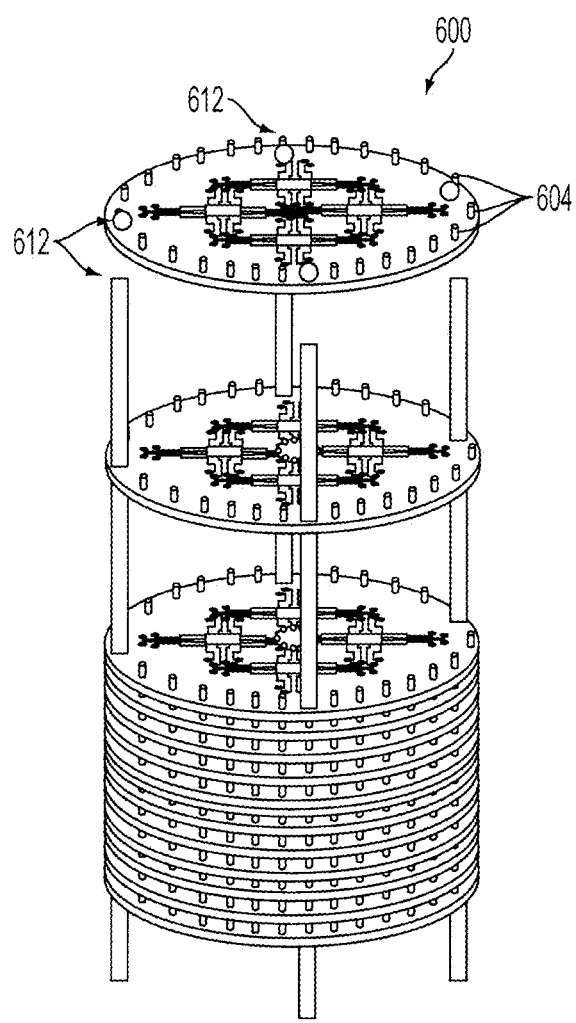

FIG. 6B illustrates an additional refinement of FIG. 6. FIG. 6B illustrates multiple keyed conductors 612, three to four in an embodiment. Conductive paths 604 are selected from materials to allow compression in a first direction (such as a vertical or height direction) which is perpendicular to the surface of each PC board in stack 600. Examples of conductive paths 604 include bent wire, spring metal bridging, soft metal deposits, or the like. Selection of other materials are possible by persons skilled in the art, and do not depart from the spirit and scope of this invention. Spacers 608 (not specifically illustrated in FIG. 6B) may be utilized to stop a compression of conductive paths 604 at a certain distance or compression pressure, and are optional depending upon the assembly process requirements. Furthermore, conductive paths 604 mate and electrically conduct to areas on the reverse side of boards 600. Any of boards 600 may electrically conduct pathway 604 directly to the opposite side, tap into and utilize signals on pathway 604 in addition to conducting to the opposite side, may process and/or re-route signals to other pathways on the opposite side, and also may not electrically conduct signals to the opposite side at all.

The assembly of stack 600 illustrated in FIG. 6B may include the following steps: (i) start with a first board 600 or another fixture that holds keyed conductors 612; (ii) place each and all of boards 600 onto keyed conductors 612 assembly in a repetitive process until all boards are within the assembly area; (iii) compress boards 600 with a predetermined pressure or final distance of compression; (iv) secure compression by connecting first and last of boards 600 to keyed conductors 612, such as with solder or welding; and (v) remove assembly 600 and trim keyed conductors 612 to flush surface.

Figure 7:
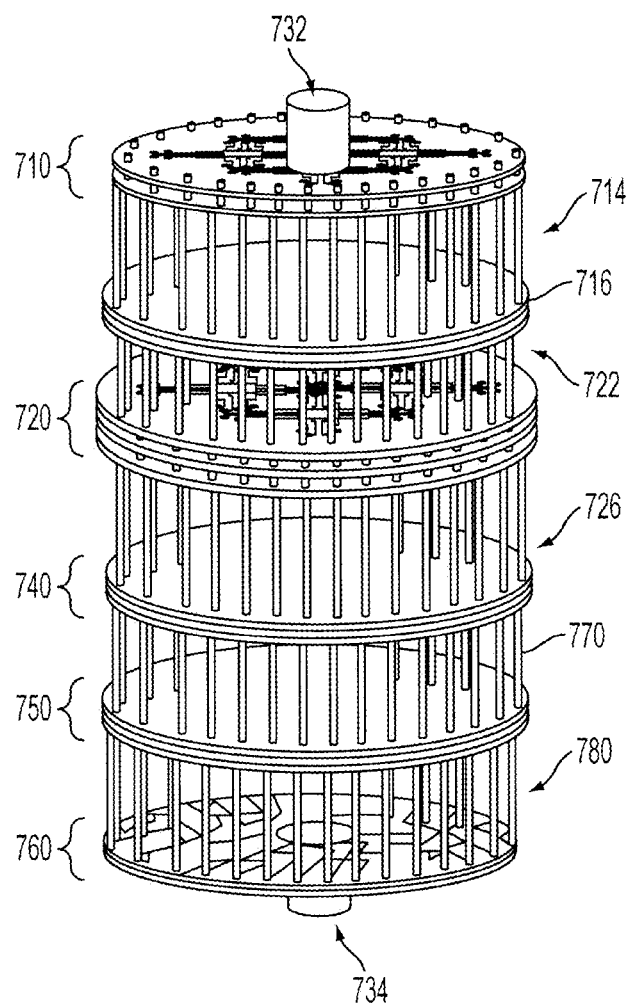

FIG. 7 illustrates mechanically and electrically coupled internal components 700 in accordance with an embodiment of the present invention. Internal components 700 include a first stack of PC boards 710, a second stack of PC boards 720, batteries 740, a first transducer 716, a second transducer 750, and a third stack of PC boards 760. The PC boards in first, second, and third stacks 710, 720, and 760 are separated from each other by spacers. First stack of PC boards 710 is mechanically and electrically coupled to first transducer 716 by outer posts 714. First transducer 716 is coupled to second stack of PC boards 720 via outer posts 722. The second stack of PC boards 720 is mechanically and electrically coupled to battery 740 by a third plurality of outer posts 726. Battery 740 is coupled to second transducer 750 via outer posts 770 and second transducer 750 is coupled to third stack of PC boards 760 via outer posts 780. First stack of PC boards 710 includes a first external conductor 732 and the third set of PC boards 760 includes a second external conductor 734. Components 700 are constructed such that external conductors 732 and 734 are not covered with potting material during construction of sensor device 104. Electrical signals and power can be sent in or out of these exposed conductors conveniently located at opposing ends of sensor device 104 after final assembly, testing, and potentially lifetime use.

C. An Example Molding Technique

Given the stack of mechanically and electrically coupled internal components (as illustrated in FIGS. 4-7), the internal components may be manufactured into a swallowable sensor device 104 using an injection molding technique as illustrated for example in FIG. 8. FIG. 8 includes injection moldings 810 that includes a plurality of cavities, such as cavity 812, as shown in FIG. 8. The cavities may have a substantially or totally circular cross-section either uniform in diameter throughout the length of cavity 812, or tapered from one end to the other of cavity 812. The base of each cavity may be substantially concave in order to manufacture an exterior housing that is capsule-shaped.

Moldings 810 and cavities 812 may contain small indentations for sensors (not shown in FIG. 8). These small indentations provide a receiving area in the hardened potting material. Use of these cavities is explained in more detail in section E below. Additionally, small indentations and/or grooves in cavities 812 may provide alignment for inserting components 832 into cavities 812.

A plurality of stacks of mechanically coupled internal components 830 is inserted into molds 810. For example, a mechanically coupled stack of internal components 832 is inserted in cavity 812. In an embodiment, each cavity of molding 810 is pre-filled with potting material 820 before inserting the internal components 830 therein. In another embodiment (not shown), the internal components 830 are inserted in molds 810, and then potting material 820 is injected therein.

In either embodiment, molds 810 are sealed with caps 840, after the internal components 830 and potting material 820 have been inserted in molds 810. For example, cap 842 seals cavity 812 after stack 832 and potting material 820 is inserted in cavity 812. As a result, potting material 820 hardens within the sealed cavities forming an exterior housing of each stack of internal components, thereby forming the swallowable sensor devices.

Importantly, however, projections included on one or more of the PC boards (such as projections 422 of PC board 220 (FIG. 4)) are not covered by the exterior housing. This is due to the distal end of each projection abutting against the side wall of each mold 810. For example, FIG. 9A illustrates a cross-sectional view of a PC board 920 inserted in cavity 812. PC board 920 may be mechanically and electrically coupled to other internal components via central post 930. PC board 920 includes a plurality of projections, such as projection 922, that extend radially outward from a central axis of PC board 920. A distal end 924 of projection 922 abuts against a side wall 934 of cavity 812. Consequently, potting material 820 included in cavity 812 is prevented from covering distal end 924 of projection 922. As set forth above and described in more detail below with reference to FIGS. 10-12, projection 922 may comprise an electrode, a hollow tubing, or a material to be removed after potting material 820 is hardened.

In another embodiment, indentations are included in side wall 934. When these indentations are aligned with projection 922, distal end 924 is exposed (not encased in potting material) but also leaves an indentation in the hardened potting material (such as indentations 1410, 1420, and/or 1430 illustrated in FIG. 14A). In this embodiment, additional sensor materials can be deposited with precision depth into the indentation for accurate building of biological/electrical sensors even after the base sensor device 104 has been created. Thus, this embodiment affords a method to customize a sensor device just prior to use, while allowing substantially short shelf life sensor materials to be utilized. In addition, each indentation may be filled with different amounts of a digestible, protective material to enable timed release of the sensor material, as described in more detail below.

In addition to projection 922, a first and second end of central post 930 abuts against a base and cap of sealed cavity 812, as illustrated in FIG. 9B. Referring to FIG. 9B, a first end 962 of central post 930 abuts against a base 854 of sealed cavity 812. Similarly, a second end 964 of central post 930 abuts against cap 842 of sealed cavity 812. Because first end 962 and second end 964 abut against the base 854 and cap 842, potting material 820 is prevented from covering first end 962 and second end 964 of central post 930. As a result, when potting material 820 hardens to form the exterior housing, first and second ends 962, 964 will be exposed to the external environment of the manufactured swallowable sensor device.

As discussed above with reference to FIG. 2A, first end 962 and second end 964 provide electrical contacts to the internal components of the swallowable sensor device. These electrical contacts can be used to test the operability of the swallowable sensor device. For example, a voltage can be applied between first and second ends 962 and 964 to energize the swallowable sensor device to initiate a self test. Results of the self test can then be transmitted to an external device. For example, the results can be transmitted to an external computing device via an acoustic communication signal (such as communication signal 106). In this way, the operability of the swallowable sensor device can be test after it is manufactured and/or before it is ingested by a patient. Furthermore, first and second ends 962 and 964 may be utilized to sense when swallowable sensor device 104 has been ingested by human 102.

D. Example Projections

As mentioned above, the projections of one or more PC boards will be exposed to the external environment of the manufactured swallowable sensor device. The projections may comprise an electrode or a hollow tubing. The electrodes may be coupled to a sensor and used to sense a condition of patient 102. The hollow tubing may be configured to deliver treatment, diagnostic aid (dye or radioactive materials), and/or to receive a sample as it travels through patient 102.

For example, FIG. 10 illustrates a PC board 1020 including a plurality of projections, such as a first hollow tubing 1032, a second hollow tubing 1036, and an electrode 1034. Each of these projections is described in more detail below.

First hollow tubing 1032 is configured to deliver treatment, such as medicine, as the swallowable sensor device travels through patient 102. A first end of first hollow tubing 1032 will be exposed to an external environment of a manufactured swallowable sensor device. In an embodiment, a second end of first hollow tubing 1032 is coupled to a container 1040. In this embodiment, container 1040 includes a medicine (or some other substance) that is to be delivered to patient 102. Circuitry on PC board 1020 is configured to cause the medicine stored in container 1040 to pass through first hollow tubing and into the external environment of the swallowable sensor device.

In an embodiment, the medicine is pressure sealed in container 1040. In this embodiment, a relatively low pressure in container 1040 keeps medicine within container 1040. At a specified time, a micro-pump 1042 increases the pressure in container 1040, thereby causing the medicine in container 1040 to pass through first hollow tubing 1032 and into the external environment. Micro-pump 1042 is controlled by circuitry contained on PC board 1020 or other circuitry contained in the swallowable sensor device.

In another embodiment, the medicine in container 1040 is prevented from passing through first hollow tubing 1032 by a blocking member (such as a gate, a membrane, a screen, or some other element). At a specified time, the blocking member is removed, thereby allowing the medicine to pass through first hollow tubing 1032 into the external environment of the swallowable sensor device. An exemplary material for blocking is a microencapsulated structure which breaks down at a certain ultrasonic frequency—such as a frequency that is equal to a frequency generated by a transducer adjacent to tubing 1032 being blocked.

A second hollow tubing 1036 is configured to receive a sample, such as a gastrointestinal fluid, as the swallowable sensor device travels through patient 102. A first end of second hollow tubing 1036 will be exposed to an external environment of a manufactured swallowable sensor device. In an embodiment, a second end of second hollow tubing 1036 is coupled to container 1040. In this embodiment, container 1040 is configured to receive the sample from the gastrointestinal tract of patient 102. Circuitry on PC board 1020 is configured to cause the sample to pass through second hollow tubing and into container 1040. For example, micro-pump 1042 may decrease the pressure in container 1040, for example by pumping out sterile water, thereby forcing the desired sample through second hollow tubing 1036 and into container 1040 through the vacuum created in the container 1040.

An embodiment of micro-pump 1042 is further depicted in FIG. 16. This embodiment is similar in nature to some inkjet printers, in that it is comprised of a chamber or tube that varies i's volume with an electrical stimulus.

Referring to FIG. 16, assembly 1600 comprises a micro-pump. Simple one directional valves 1610 allow flow of fluids from one side of assembly 1600 (e.g., the right side) to the other side of assembly 1600 (e.g., the left side). Furthermore, valve 1610 is detailed as an assembly of a base 1612, with an orifice 1614 that is covered by material 1616, which is in turn attached to the base by a hinge 1618. The valve assembly 1610 is one configuration of many possibilities depending upon the desired characteristics related to in part fluid density, flow capability, and the frequency of expansion and contraction of the chamber 1650. Alternate embodiments of the valve assembly 1610 do not depart from the spirit and scope of this invention.

Tube 1620 (e.g., the chamber of micro-pump 1042) expands and contracts upon a charge deposited by electrical wiring 1630. A common material for tube 160 (as used, for example, in some ink jet printers) is a piezoelectric material, such as PZT. An example configuration is depicted in FIG. 16, whereby one of electrical attachments 1630 conducts through the wall of tubing 1620 and to the inside conductive surface through a via 1640. When electrical charges on conductors 1630 are altered, the volume 1650 of the inside of the tube 1620 will also alter. A pumping action is a resultant of the expansion and contraction of the volume 1650 in combination with the valves 1610 that allow expansion of fluid to flow from the right, and contraction by allowing fluid to flow to the left. The frequency and voltage of the electrical charge alterations will control the rate of the fluid flow, and can be categorized by timing, frequency, current and the like to a certain volume of liquid pumped through the assembly 1600. FIG. 16 depicts merely one of a multitude of potential embodiments of micro-pump 1042. One skilled in the art would recognize micro-pump 1042 could be manufactured in many different ways, such as micro-impellers and MEMs structures without departing from the spirit and scope of this invention.

Electrode 1034 is configured to be coupled to a sensor that senses a condition of patient 102. FIG. 11 illustrates an example sensor 1102. Sensor 1102 includes a culture area 1104 that includes a type of culture material. The culture material is configured to chemically react to specific stimuli within the gastrointestinal tract of patient 102. Based on the chemical reaction, sensor 1102 sends a signal to the internal circuitry of the swallowable sensor device via electrode 1034. The signal may then be sent to an external entity as described above. FIG. 12 illustrates an embodiment of swallowable sensor device 104 including a plurality of sensors 1202 that are exposed to the external environment of swallowable sensor device 104—i.e., sensors 1202 are not contained within housing 108.

E. Example Sensor Implementations

An example application for using swallowable sensor device 104 in combination with biological sensor materials is described below. As previously mentioned, FIG. 8 depicts cavities 812 and electrical components 832. In the below-described example, cavity 812 includes indentations aligning with inserted components 832 such that the indentation abuts distal end 924 of projection 922 (see FIG. 9A). Upon hardening of potting material 820, the indentations of cavities 812 leave similar indentations in the hardened potting material 820, and an exposed distal end 924 of projection 922. The indentations may be either localized with a defined area for each projection 922 (circular, oval, etc), or indentations may run an entire length of the cavity 812, and they may also define a localized area running between multiple projections 922 on same or different boards of components 832. The resulting indentation can be of precise depth and volume.

FIGS. 14A-D depict embodiments of swallowable sensor device 104 having a plurality of indentations. FIG. 14A is an end view depicting swallowable sensor device 104 including, for example, three indentations—at sites 1410, 1420, and 1430. As shown, site 1410 and 1420 have multiple projections 922 into each indentation, while 1430 has only one projection. An exemplary implementation for site 1410 comprises electrical contacts for both projections 922. However, an exemplary implementation for site 1430 comprises an electronic sensor package (for example, an ion sensitive field effect transistor (ISFET) based pH sensor) affixed to the end of projection 922.

In an embodiment, a sensor material 1440 (FIG. 14D) in gel or paste form can be placed into the sites 1410, 1420, 1430 by simply applying a rubber scraping type of tool similar to filling a hole in plaster with a putty knife. A number of methods could be employed to fill one, many, or all sites with the same or different sensor materials 1440. In an embodiment, sensor material 1440 is an enzyme material. Furthermore, a heme oxygenase enzyme material is preferred for detection of blood within the gastrointestinal tract. In another embodiment, an enzymatic material that reacts with a CarcinoEmbryonicAntigen (CEA) effect detection of cancerous growth in the gastrointestinal tract. The capability of sensor device 104 to detect the presence of blood or cancerous growth in combination with the ability to detect the precise location of sensor device 104 provides a doctor and patient information not available in any other convenient diagnostic. Example methods for precisely locating sensor device 104 are described in U.S. Provisional Patent Application 60/842,360 to Arneson et al., entitled "Swallowable Low Power Sensor Device and System for Communicating with Same" and filed Sep. 6, 2006, and in U.S. Provisional Patent Application 60/924,928 to Arneson et al., entitled "Imaging and Locating Systems and Methods for a Swallowable Sensor Device" and filed Jun. 5, 2007. The entirety of each of the foregoing applications is incorporated by reference herein. After application of sensor material 1440, the resultant surface of site 1410, 1420, and 1430 is flush with the rest of sensor device 104.

F. Timed Release Sensor Material

An embodiment of the present invention enables timed release of sensor material 1440 based on a thickness of a protective layer, as described in more detail below.

The enzymatic sensor material 1440 does not function long while exposed to a harsh environment (such as the stomach acid, and in general, the digestive system itself). Accordingly, a protective layer 1450 can be used to protect sensor material 1440. Importantly, the thickness of protective layer 1450 can be manufactured to enable sensor material 1440 to be exposed at specific times and/or locations as swallowable sensor device 104 travels through the digestive system of human 102.

To provide this feature, an embodiment of sensor device 104 includes a plurality of sensors 202, each having sensor material 1440 and a layer of protecting material 1450A, B, C, wherein the layers of protecting material 1450 have differing thickness or density to expose sensor material 1440 of each sensor 202 at different times as sensor device 104 travels through human 102. Protecting material 1450 may comprise known types of digestible materials, such as known timed release medicines available over-the-counter, as would be apparent to a person skilled in the relevant art(s). For example, a thickness of material 1450A may expose sensor material 1440 to a stomach environment after 30 minutes, while a thickness of material 1450B may expose sensor material 1440 to a small intestine environment after 1 hour. Given a sensor material functional life span of 30 minutes, and a desired operational time for sensor device 104 of approximately 24 hours, for example, then embodiments of the present invention include 48 (or more) different thicknesses for protective layer 1450.

An embodiment of this present invention creates sensor device 104 from a cavity 812 that has a tapered portion of the length of the cavity, as illustrated for example in FIG. 14B. The resultant shape of the hardened potting materials produces a tapered assembly. The tapered assembly is applied to a consistent diameter mold or apparatus that applies a digestible material to the assembly. The result is a tapered thickness 1450 of digestible material covering sensor material 1440. In this method, sensor materials 1440 of swallowable sensor device 104 are time released to the environment, and at a rate whereby at least one of sensors 202 is active at any point in time throughout a desired period of time (such as approximately 24 hours, which is an average time for swallowable sensor device 104 to pass through human 102).

In an alternate embodiment, sensor material 1440 can be applied at a uniform thickness, such as with a uniform spray technique, into a site 1410, 1420, and 1430 of different thickness and volume, as illustrated for example in FIG. 14C. In another part of a process, digestible material 1450 can be applied so as to fill the remainder of the volume of sites 1410, 1420, and 1430. The result is similar to the tapered example, in that a sensor material 1440 is covered by digestible materials 1450 of varying thicknesses.

Figure 15A:
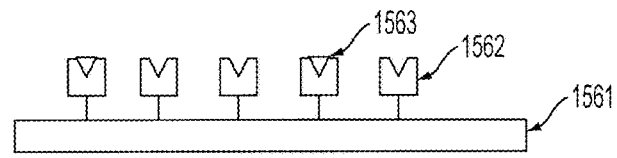
Figure 15B:
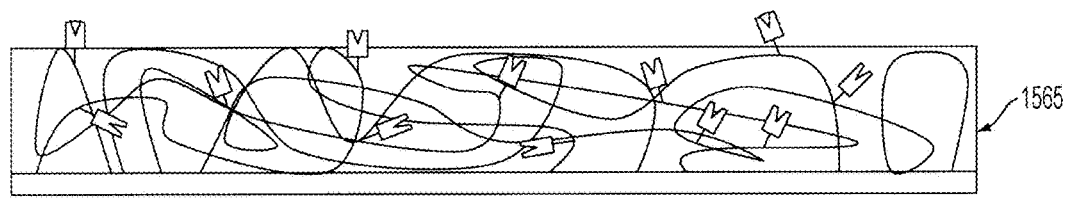
Figure 15C:
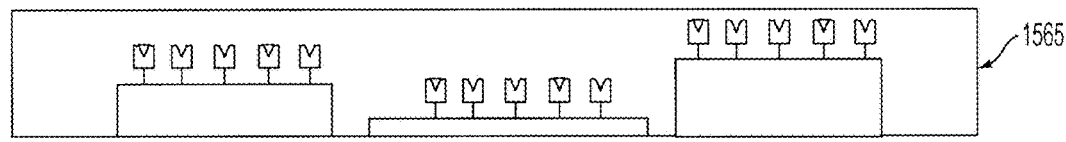
Figure 15D:
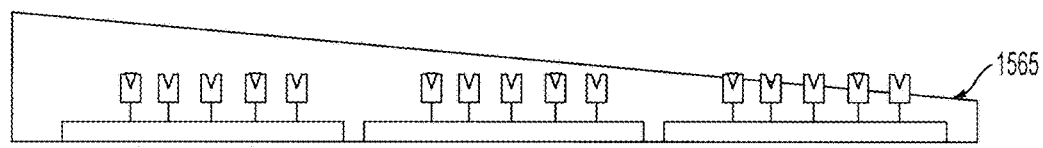

FIGS. 15A-D depict several embodiments of timed release biological sensor materials 1440. FIG. 15A depicts an example timed release embodiment. A sensor comprises an electrically conductive material 1561, upon which an antibody 1562 is affixed. In general, a digestible material 1565 covers antibody 1562 with different depths for exposure to a potential antigen 1563 in a timed release fashion. FIG. 15B depicts a randomly distributed mixture of antibodies within a digestible material, for example a polymer matrix. FIG. 15C depicts an example of different depth indentations of 1410, 1420, and 1430 depicted to FIG. 14. FIG. 15D depicts a further embodiment illustrating a fixed depth indentation with a tapered depth digestible material 1565.

F. Example Testing Methods

Ingestible, pill-formed and packaged electronic products are a new concept. Although packaging and production of electronics is well-known and packaging and production of medicine is well-known, a process that combines both provides some interesting issues. Final testing of production pieces of electronics and resultant packaging can be done in a delicate environment, preserved with electrostatic bags and other protective packaging. Medicines also have a delicate environment for biological sensitivity, but not for electrical sensitivity. Thus, a process for a combination of packaging and testing of ingestible electronic devices is a new requirement, and an object of this present invention.

FIGS. 17A and 17B respectively depict a top view and a side view of an assembly 1700. Assembly 1700 comprises an industry typical package 1710 (such as a heat formable plastic) and electrical pathways 1720. The package material 1710 is modified from a typical approach with electrical pathways 1720. Specifically, electrical pathways 1720 start from an edge accessible connection point 1740, and terminate internally at connection points 1730. Importantly, electrical pathways 1720 remain in a flat state as depicted in FIGS. 17A and 17B. Depending upon cost, speed, complexity, and a type of electrical signal carried, electrical pathways 1720 may comprise copper, aluminum, a silver paste, or some other conductive material as would be apparent to a person skilled in the relevant art(s). Additionally, the conductive material may be applied to package material 1710 in a process such as printing, a subtractive or additive process such as is typical in circuit board manufacturing, and also a foil cut and adhesive process also typically found in a printing/packaging industry. A person skilled in the art would understand how to select a material and method of conductive pathways 1720 that would deliver both electrical performance necessary, while achieving desired volume and cost goals. Selection of additional materials and methods for affixing these materials to package 1710 does not depart from the spirit and scope of this invention. In another embodiment, edge accessible connection points 1740 may be located on both sides of assembly 1700 as would be apparent to a person skilled in the art.

Figure 17D:
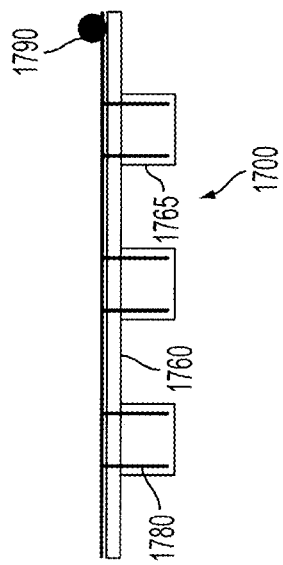
Figure 17C:
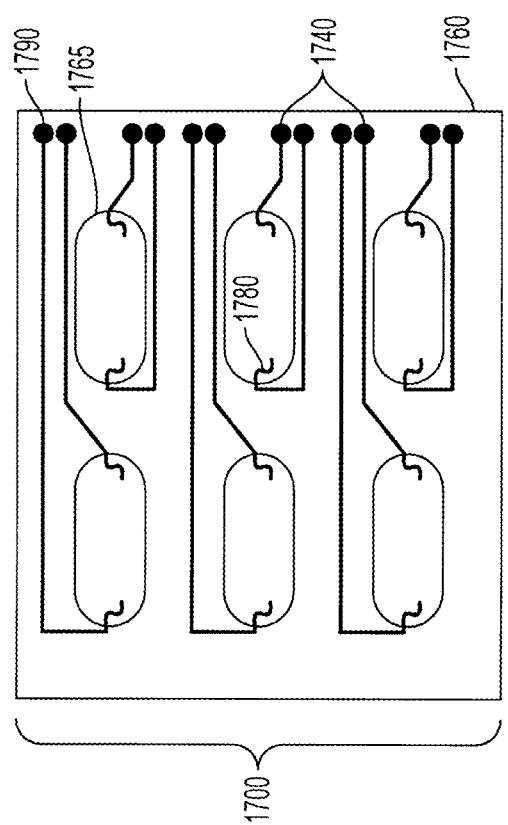

Assembly 1700 is then introduced into a mold, with heat and some form of pressure common with the molding of plastic packaging. The mold causes wells 1765 to be formed in assembly 1700, as depicted in FIGS. 17C and 17D. Wells 1765 are created of the shape and size to deposit an ingestible electronic device such as device 104 of FIG. 1. In the molding process, connection points 1730 change shape to become three dimensional pathways 1780 extending into well 1765, while retaining their electrical conductivity. Optionally, an edge connection point 1740 may transform into a heightened external connection point 1790 in the final form. Assembly 1700 now provides a convenient electrical connection point 1790, carrying electrical signals through pathways to a point 1780 on the package that now electrically connects to programming and/or test points on ingestible device 104 that can be deposited into well 1765.

FIGS. 18A and 18B respectively illustrate a top view and a side view of a machine that deposits ingestible electronic devices 1890 (such as device 104 of FIG. 1) into wells 1765 of assembly 1700. As assembly 1700 moves in a conveyor-belt fashion, a mechanism 1820 directs one device 1890 at a time from feeder 1810 and applies a slight pressure on device 1890 to urge it into one of wells 1765. When urged into a well 1765, test points 1895 on device 1890 are then electrically connected to connection points 1830 of assembly 1700. As shown in FIG. 18, final assembly 1850 results in electrical connection points 1830 that are conductive to electronic devices in the assembly. In a final packaging, assembly 1850 may be covered by a film or label in order to contain the devices 1890 and/or provide biological containment or isolation from a non-sterile distribution environment. The film or label is applied such that electrical connection points 1830 are not electrically insulated, for example with a shorter width label than the width of assembly 1850. Furthermore, upon testing completion, electrical connection points 1830 may be removed, or trimmed at a factory, by simply cutting this edge from the final packaging.

Assembly 1850 illustrates the capability to both biologically contain an ingestible electronic device while facilitating direct electrical connection for a variety of testing, programming, and energy transfer (for example, battery charging) functions while not requiring all of the test platforms and environments within and between to be sterilized and/or germ free. Furthermore, as depicted in FIG. 18, final assembly 1850 allows individual testing of devices 1890, either sequentially or in parallel. A person skilled in the relevant art(s) would understand how to develop a test platform external, but applied, to assembly 1850 that tests, programs, charges, and verifies each of a multitude of devices 1890 within the assembly serially, in parallel, or any combination thereof. Such test devices are hereby conceived and do not depart from the spirit and scope of the present invention.

In an alternate embodiment, test points 1895 can be electronically connected through conductive pathways 1720 and 1730, with optional additional electronic components and/or power supplies deposited upon package material 1710. In this embodiment, the removal of electronic device 1890 from assembly 1850 is detectable or determinable. Upon removal, electronic device 1890 can be configured to autonomously prepare for subsequent ingestion within an animal or human, for example by turning one or more features and functions.

Layered Structure

In an embodiment, swallowable sensor device 104 has a layered structure to provide efficient transfer of sound energy into the surrounding medium (e.g., liquid, solid, human tissue or viscoelastic materials). Each layer or composite layers has a particular acoustic impedance. The material closest to the sensor has an acoustic impedance that is a large percentage of the sensor. As the material or material layers transition to the outside of swallowable sensor device 104, the fractional percentage of the material's acoustic impedance drops to match the surrounding medium. The change in material properties can be accomplished by multiple layers of materials (FIG. 19) or by a single anisotropic material having a distributed impedance or density (FIG. 20).

FIG. 19 illustrates an embodiment in which the change in material properties of swallowable sensor device 104 is accomplished by multiple layers of materials. As illustrated in FIG. 19, swallowable sensor device 104 includes an acoustic sensor 1901, an intermediate layer 1903, and an outer layer 1905. Acoustic sensor 1901 comprises a transducer that converts mechanical energy into electrical energy, and vice versa. Intermediate layer 1903 is configured to have an impedance similar to the acoustic impedance of acoustic sensor 1901. And, outer layer 1905 is configured to have an impedance similar to the acoustic impedance of the external environment. Intermediate layer 1903 and outer layer 1905 may be layered with additional materials to their characteristics. For example, intermediate layer 1903 can be configured to be harder than outer layer 1905. Although swallowable sensor device 104 as illustrated in FIG. 19 includes only intermediate layer 1903 and outer layer 1905, it is to be appreciated that additional layers may be included on swallowable sensor device 104. The layers of swallowable sensor device 104, illustrated in FIG. 19, may be applied using mechanical, electrical, magnetic, and/or chemical fastening. For example, the various layers of material may be disposed on swallowable sensor device 104 through an injection molding process. As another example, the various layers may be disposed on swallowable sensor device 104 through a dip coating process, wherein swallowable sensor device 104 is successively dipped in one or more vats of materials (such as latex) to achieve the appropriate acoustic layering.

FIG. 20 illustrates an embodiment in which the change in material properties of swallowable sensor device 104 is accomplished by a single anisotropic material (distributed impedance or density) according to an embodiment of the present invention. As illustrated in FIG. 20, swallowable sensor device 104 includes an acoustic sensor 2001 and an anisotropic layer 2003. Acoustic sensor 2001 is a transducer that converts mechanical energy to electrical energy, and vice versa. Anisotropic layer 2003 has an acoustic impedance that various with distance—such that the inner portions of anisotropic layer 2003 have an acoustic impedance similar to acoustic sensor 2001, whereas the outer portions of anisotropic layer 2003 have an acoustic impedance similar to the external environment.

In an embodiment, the anisotropic layer 2003, illustrated in FIG. 20, is manufactured using a UV epoxy (such as potting material 820) in an oxygen-rich environment. The oxygen inhibits the UV cure. Consequently, if the layer 2003 is UV cured in an oxygen-rich environment, the outer portions of layer 2003 will not be cured as much as the inner layers. The amount of oxygen in the environment can be controlled to cause the acoustic impedance of the exterior of anisotropic layer 2003 to substantially match the acoustic impedance of human or animal tissue, while the inner portions of layer 2003 will be UV cured to substantially match the acoustic impedance of acoustic sensor 2001.

Example Computer System Embodiments

According to an example embodiment, a swallowable sensor device may execute computer-readable instructions to perform its functions. Furthermore, a sensor link module for communicating with the swallowable sensor device may execute computer-readable instructions to communicate with the swallowable sensor device. Still further, a computing device may execute computer-readable instructions to control and communicate with the swallowable sensor device and/or the sensor link module, and/or to process data obtained by the swallowable sensor device and/or sensor link module, as described above. Still further, a test kit and medical diagnostic network system may each execute computer-readable instructions to perform its functions.

In one embodiment, one or more computer systems are capable of carrying out the functionality described herein. An example of a computer system 1300 is shown in FIG. 13.

The computer system 1300 includes one or more processors, such as processor 1304. The processor 1304 is connected to a communication infrastructure 1306 (e.g., a communications bus, cross-over bar, or network). Various software embodiments are described in terms of this exemplary computer system. After reading this description, it will become apparent to a person skilled in the relevant art(s) how to implement the invention using other computer systems and/or architectures.

Computer system 1300 can include a display interface 1302 that forwards graphics, text, and other data from the communication infrastructure 1306 (or from a frame buffer not shown) for display on the display unit 1330.

Computer system 1300 also includes a main memory 1308, preferably random access memory (RAM), and may also include a secondary memory 1310. The secondary memory 1310 may include, for example, a hard disk drive 1312 and/or a removable storage drive 1314, representing a floppy disk drive, a magnetic tape drive, an optical disk drive, etc. The removable storage drive 1314 reads from and/or writes to a removable storage unit 1318 in a well known manner. Removable storage unit 1318 represents a floppy disk, magnetic tape, optical disk, etc. which is read by and written to by removable storage drive 1314. As will be appreciated, the removable storage unit 1318 includes a computer usable storage medium having stored therein computer software and/or data.

In alternative embodiments, secondary memory 1310 may include other similar devices for allowing computer programs or other instructions to be loaded into computer system 1300. Such devices may include, for example, a removable storage unit 1322 and an interface 1320. Examples of such may include a program cartridge and cartridge interface (such as that found in video game devices), a removable memory chip (such as an erasable programmable read only memory (EPROM), or programmable read only memory (PROM)) and associated socket, and other removable storage units 1322 and interfaces 1320, which allow software and data to be transferred from the removable storage unit 1322 to computer system 1300.

Computer system 1300 may also include a communications interface 1324. Communications interface 1324 allows software and data to be transferred between computer system 1300 and external devices. Examples of communications interface 1324 may include a modem, a network interface (such as an Ethernet card), a communications port, a Personal Computer Memory Card International Association (PCMCIA) slot and card, etc. Software and data transferred via communications interface 1324 are in the form of signals 1328 which may be electronic, electromagnetic, optical or other signals capable of being received by communications interface 1324. These signals 1328 are provided to communications interface 1324 via a communications path (e.g., channel) 1326. This channel 1326 carries signals 1328 and may be implemented using wire or cable, fiber optics, a telephone line, a cellular link, a radio frequency (RF) link and other communications channels.

In this document, the terms "computer program medium" and "computer usable medium" are used to generally refer to media such as removable storage drive 1314 and a hard disk installed in hard disk drive 1312. These computer program products provide software to computer system 1300. The invention is directed to such computer program products.

Computer programs (also referred to as computer control logic) are stored in main memory 1308 and/or secondary memory 1310. Computer programs may also be received via communications interface 1324. Such computer programs, when executed, enable the computer system 1300 to perform the features of the present invention, as discussed herein. In particular, the computer programs, when executed, enable the processor 1304 to perform the features of the present invention. Accordingly, such computer programs represent controllers of the computer system 1300.

In an embodiment where the invention is implemented using software, the software may be stored in a computer program product and loaded into computer system 1300 using removable storage drive 1314, hard drive 1312 or communications interface 1324. The control logic (software), when executed by the processor 1304, causes the processor 1304 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

CONCLUSION

Methods and systems for manufacturing a swallowable sensor device have been presented. Example embodiments described above relate to a human subject. This is for illustrative purposes, and not limitation. Embodiments of the present invention are applicable to other types of animals, including livestock (cattle, sheep, pigs, chickens, turkeys, ostriches, etc.), pets (e.g., dogs, cats, horses, etc.), and other animals of interest such as race horses or other performance/sport animals. Such applicability to these types of animals, and other types, will be apparent to persons skilled in the relevant art(s) from the teachings herein, and is within the scope and spirit of embodiments of the present invention.

Furthermore, example embodiments described above relate to passing a swallowable sensor device through a gastrointestinal tract, for illustrative purposes. However, embodiments of the present invention are applicable to further bodily systems other than the gastrointestinal tract, including the circulatory system, the urinary tract, and other bodily systems and additionally other means of entry or implant into a body cavity of an animal or human. Such applicability to other types of bodily systems will be apparent to persons skilled in the relevant art(s) from the teachings herein, and is within the scope and spirit of embodiments of the present invention.

In addition, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner.

Moreover, it is to be appreciated that the Detailed Description section, and not the Abstract section, is intended to be used to interpret the claims. The Abstract section may set forth one or more but not all exemplary embodiments of the present invention as contemplated by the inventor(s), and thus, is not intended to limit the present invention and the appended claims in any way.

What is claimed is:

1. A system for manufacturing a swallowable sensor device, comprising:
    means for mechanically coupling a plurality of internal components of the swallowable sensor device, wherein the plurality of internal components includes a printed circuit (PC) board having a plurality of projections extending radially outward;
    means for filling a cavity with a potting material;
    means for inserting the mechanically coupled components into the cavity, a distal end of each projection abutting against a side wall of the cavity thereby preventing the potting material from covering the distal end of each projection; and
    means for sealing the cavity with a cap, wherein the potting material hardens within the sealed cavity to form a housing of the swallowable sensor device such that the distal end of each projection is exposed to an external environment of the swallowable sensor device.

2. The system of claim 1, wherein the means for filling the cavity comprises means for filling the cavity with the potting material before inserting the mechanically coupled components therein.

3. The system of claim 1, wherein the means for filling the cavity comprises means for filling the cavity with the potting material after inserting the mechanically coupled components therein.

4. The system of claim 1, wherein the means for mechanically coupling the plurality of internal components comprises a post.

5. The system of claim 4, wherein a first end of the post abuts against a base of the cavity and a second end of the post abuts against the cap thereby preventing the potting material from covering the first and second ends of the post.

6. The system of claim 5, further comprising:
    means for providing a voltage between the first and second ends of the post to test operability of the swallowable sensor device.

7. The system of claim 4, wherein the post provides an electrical coupling between the plurality of internal components.

8. The system of claim 4 wherein the post comprises a transducer configured to convert electrical energy to mechanical energy.

9. The system of claim 4, wherein the plurality of internal components are annularly-shaped and mechanically coupled by the post along a common central axis.

10. The system of claim 1, wherein at least one of the projections comprises an electrode, and the system further comprises means for electrically coupling a sensor to the electrode.

11. The system of claim 1, wherein at least one of the projections comprises a hollow tubing coupled to a container, wherein the container is included inside the housing of the swallowable sensor device.

12. The system of claim 1, wherein the plurality of internal components includes a battery.

13. The system of claim 1, wherein the plurality of internal components includes a transducer that is configured to convert electrical energy to mechanical energy.

* * * * *